US009974647B2

(12) United States Patent
Ganesan et al.

(10) Patent No.: US 9,974,647 B2
(45) Date of Patent: May 22, 2018

(54) TWO STAGE ANCHOR AND MITRAL VALVE ASSEMBLY

(71) Applicant: Caisson Interventional, LLC, Maple Grove, MN (US)

(72) Inventors: Kavitha Ganesan, Maple Grove, MN (US); Ramji T. Venkatasubramanian, Maple Grove, MN (US); Andrew T. Forsberg, Plymouth, MN (US); Alex A. Peterson, Maple Grove, MN (US); Cyril J. Schweich, Jr., Maple Grove, MN (US); Todd J. Mortier, Mound, MN (US)

(73) Assignee: Caisson Interventional, LLC, Maple Grove, MN (US)

( * ) Notice: Subject to any disclaimer, the term of this patent is extended or adjusted under 35 U.S.C. 154(b) by 41 days.

(21) Appl. No.: 14/674,691

(22) Filed: Mar. 31, 2015

(65) Prior Publication Data

US 2015/0359629 A1 Dec. 17, 2015

Related U.S. Application Data

(60) Provisional application No. 62/011,164, filed on Jun. 12, 2014.

(51) Int. Cl.
*A61F 2/24* (2006.01)
(52) U.S. Cl.
CPC .......... *A61F 2/2409* (2013.01); *A61F 2/2412* (2013.01); *A61F 2/2418* (2013.01); *A61F 2/2427* (2013.01); *A61F 2/2436* (2013.01); *A61F 2250/006* (2013.01)

(58) Field of Classification Search
CPC ........ A61F 2/2409; A61F 2/24; A61F 2/2418; A61F 2/2448; A61F 2/2463; A61F 2/2469; A61F 2/2436; A61F 2/2427; A61F 2/2412
See application file for complete search history.

(56) References Cited

U.S. PATENT DOCUMENTS

| 4,680,031 | A | 7/1987 | Alonso |
| 5,423,887 | A | 6/1995 | Love et al. |
| 5,662,704 | A | 9/1997 | Gross |
| 5,855,601 | A | 1/1999 | Bessler et al. |
| 5,984,959 | A | 11/1999 | Robertson et al. |
| 6,113,631 | A | 9/2000 | Jansen |
| 6,296,662 | B1 | 10/2001 | Caffey |
| 6,309,417 | B1 | 10/2001 | Spence et al. |

(Continued)

FOREIGN PATENT DOCUMENTS

| EP | 350302 | 1/1990 |
| EP | 0592410 | 4/1994 |

(Continued)

OTHER PUBLICATIONS

US 9,532,869, 01/2017, Quadri et al. (withdrawn)

(Continued)

*Primary Examiner* — Jocelin Tanner
(74) *Attorney, Agent, or Firm* — Fish & Richardson P.C.

(57) ABSTRACT

Systems and methods for medical interventional procedures, including approaches to valve implantation. In one aspect, the methods and systems involve a modular approach to mitral valve therapy.

20 Claims, 29 Drawing Sheets

(56) References Cited

U.S. PATENT DOCUMENTS

| | | |
|---|---|---|
| 6,332,893 B1 | 12/2001 | Mortier et al. |
| 6,358,277 B1 | 3/2002 | Duran |
| 6,425,916 B1 | 7/2002 | Garrison et al. |
| 6,530,952 B2 | 3/2003 | Vesely |
| 6,569,196 B1 | 5/2003 | Vesely |
| 6,582,462 B1 | 6/2003 | Andersen et al. |
| 6,629,534 B1 | 10/2003 | St. Goar et al. |
| 6,730,118 B2 | 5/2004 | Spenser et al. |
| 6,730,121 B2 | 5/2004 | Ortiz et al. |
| 6,767,362 B2 | 7/2004 | Schreck |
| 6,769,434 B2 | 8/2004 | Liddicoat et al. |
| 6,790,229 B1 | 9/2004 | Berreklouw |
| 6,883,522 B2 | 4/2005 | Spence et al. |
| 6,893,459 B1 | 5/2005 | Macoviak |
| 6,893,460 B2 | 5/2005 | Spenser et al. |
| 6,908,481 B2 | 6/2005 | Cribier |
| 6,949,122 B2 | 9/2005 | Adams et al. |
| 7,011,681 B2 | 3/2006 | Vesely |
| 7,018,406 B2 | 3/2006 | Seguin et al. |
| 7,044,966 B2 | 5/2006 | Svanidze et al. |
| 7,101,396 B2 | 9/2006 | Artof et al. |
| 7,147,663 B1 | 12/2006 | Berg et al. |
| 7,160,322 B2 | 1/2007 | Gabbay |
| 7,175,656 B2 | 2/2007 | Khairkhahan |
| 7,217,287 B2 | 5/2007 | Wilson et al. |
| 7,252,682 B2 | 8/2007 | Seguin |
| 7,320,704 B2 | 1/2008 | Lashinski et al. |
| 7,329,278 B2 | 2/2008 | Seguin et al. |
| 7,381,218 B2 | 6/2008 | Schreck |
| 7,381,220 B2 | 6/2008 | Macoviak et al. |
| 7,393,360 B2 | 7/2008 | Spenser et al. |
| 7,442,204 B2 | 10/2008 | Schwammenthal et al. |
| 7,503,930 B2 | 3/2009 | Sharkawy et al. |
| 7,510,575 B2 | 3/2009 | Spenser et al. |
| 7,524,330 B2 | 4/2009 | Berreklouw |
| 7,524,331 B2 | 4/2009 | Birdsall |
| 7,578,843 B2 | 8/2009 | Shu |
| 7,585,321 B2 | 9/2009 | Cribier |
| 7,597,711 B2 | 10/2009 | Drews et al. |
| 7,618,446 B2 | 11/2009 | Andersen et al. |
| 7,625,403 B2 | 12/2009 | Krivoruchko |
| 7,632,308 B2 | 12/2009 | Loulmet |
| 7,708,775 B2 | 5/2010 | Rowe et al. |
| 7,717,955 B2 | 5/2010 | Lane et al. |
| 7,722,666 B2 | 5/2010 | Lafontaine |
| 7,727,276 B2 | 6/2010 | Machiraju |
| 7,748,389 B2 | 7/2010 | Salahieh et al. |
| 7,776,083 B2 | 8/2010 | Vesely |
| 7,780,725 B2 | 8/2010 | Haug et al. |
| 7,785,364 B2 | 8/2010 | Styrc |
| 7,837,727 B2 | 11/2010 | Goetz et al. |
| 7,896,915 B2 | 3/2011 | Guyenot et al. |
| 7,914,569 B2 | 3/2011 | Nguyen et al. |
| 7,935,144 B2 | 5/2011 | Robin et al. |
| 7,947,072 B2 | 5/2011 | Yang et al. |
| 7,947,075 B2 | 5/2011 | Goetz et al. |
| 7,959,672 B2 | 6/2011 | Salahieh et al. |
| 7,981,153 B2 | 7/2011 | Fogarty et al. |
| 7,988,725 B2 | 8/2011 | Gross et al. |
| 8,016,882 B2 | 9/2011 | Macoviak et al. |
| 8,025,695 B2 | 9/2011 | Fogarty et al. |
| 8,048,153 B2 | 11/2011 | Salahieh et al. |
| 8,052,749 B2 | 11/2011 | Salahieh et al. |
| 8,055,360 B2 | 11/2011 | Park et al. |
| 8,057,540 B2 | 11/2011 | Letac et al. |
| 8,062,355 B2 | 11/2011 | Figulla et al. |
| 8,092,518 B2 | 1/2012 | Schreck |
| 8,092,521 B2 | 1/2012 | Figulla et al. |
| 8,092,524 B2 | 1/2012 | Nugent et al. |
| 8,123,801 B2 | 2/2012 | Milo |
| 8,133,270 B2 | 3/2012 | Kheradvar et al. |
| 8,142,492 B2 | 3/2012 | Forster et al. |
| 8,157,852 B2 | 4/2012 | Bloom et al. |
| 8,157,853 B2 | 4/2012 | Laske et al. |
| 8,163,011 B2 | 4/2012 | Rankin |
| 8,172,898 B2 | 5/2012 | Alferness et al. |
| 8,182,528 B2 | 5/2012 | Salahieh et al. |
| 8,182,530 B2 | 5/2012 | Huber |
| 8,206,437 B2 | 6/2012 | Bonhoeffer et al. |
| 8,231,670 B2 | 7/2012 | Salahieh et al. |
| 8,236,049 B2 | 8/2012 | Rowe et al. |
| 8,246,677 B2 | 8/2012 | Ryan |
| 8,252,051 B2 | 8/2012 | Chau et al. |
| 8,262,724 B2 | 9/2012 | Seguin et al. |
| 8,273,120 B2 | 9/2012 | Dolan |
| 8,277,502 B2 | 10/2012 | Miller et al. |
| 8,282,051 B2 | 10/2012 | Nutaro et al. |
| 8,287,591 B2 | 10/2012 | Keidar et al. |
| 8,292,938 B2 | 10/2012 | Case |
| 8,308,796 B2 | 11/2012 | Lashinski et al. |
| 8,308,798 B2 | 11/2012 | Pintor et al. |
| 8,317,858 B2 | 11/2012 | Straubinger et al. |
| 8,323,332 B2 | 12/2012 | Agnew |
| 8,323,335 B2 | 12/2012 | Rowe et al. |
| 8,348,998 B2 | 1/2013 | Pintor et al. |
| 8,403,983 B2 | 3/2013 | Quadri et al. |
| 8,449,599 B2 | 5/2013 | Chau et al. |
| 8,454,686 B2 | 6/2013 | Alkhatib |
| 8,460,366 B2 | 6/2013 | Rowe |
| 8,500,798 B2 | 8/2013 | Rowe et al. |
| 8,512,398 B2 | 8/2013 | Alkhatib |
| 8,512,399 B2 | 8/2013 | Lafontaine |
| 8,568,477 B2 | 10/2013 | Lashinski et al. |
| 8,579,964 B2 | 11/2013 | Lane et al. |
| 8,585,755 B2 | 11/2013 | Chau et al. |
| 8,623,080 B2 | 1/2014 | Fogarty et al. |
| 8,628,569 B2 | 1/2014 | Benichou et al. |
| 8,628,571 B1 | 1/2014 | Hacohen et al. |
| 8,632,586 B2 | 1/2014 | Spenser et al. |
| 8,641,757 B2 | 2/2014 | Pintor et al. |
| 8,652,203 B2 | 2/2014 | Quadri et al. |
| 8,657,872 B2 | 2/2014 | Seguin |
| 8,685,085 B2 | 4/2014 | Guyenot et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,795,355 B2 | 8/2014 | Alkhatib |
| 8,795,356 B2 | 8/2014 | Quadri et al. |
| 8,808,371 B2 | 8/2014 | Cartledge |
| 8,834,564 B2 | 9/2014 | Tuval et al. |
| 8,840,662 B2 | 9/2014 | Salahieh et al. |
| 8,840,663 B2 | 9/2014 | Salahieh et al. |
| 8,845,720 B2 | 9/2014 | Conklin |
| 8,852,272 B2 | 10/2014 | Gross et al. |
| 8,858,620 B2 | 10/2014 | Salahieh et al. |
| 8,870,948 B1 | 10/2014 | Erzberger et al. |
| 8,870,949 B2 | 10/2014 | Rowe |
| 8,876,895 B2 | 11/2014 | Tuval et al. |
| 8,894,702 B2 | 11/2014 | Quadri et al. |
| 8,911,493 B2 | 12/2014 | Rowe et al. |
| 8,926,690 B2 | 1/2015 | Kovalsky |
| 8,926,691 B2 | 1/2015 | Chau et al. |
| 8,932,358 B1 | 1/2015 | Nehls |
| 8,961,595 B2 | 2/2015 | Alkhatib |
| 8,968,395 B2 | 3/2015 | Hauser et al. |
| 8,986,370 B2 | 3/2015 | Southerland et al. |
| 8,986,373 B2 | 3/2015 | Chau et al. |
| 9,005,277 B2 | 4/2015 | Pintor et al. |
| 9,005,278 B2 | 4/2015 | Pintor et al. |
| 9,017,399 B2 | 4/2015 | Gross et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,050,188 B2 | 6/2015 | Schweich et al. |
| 9,066,801 B2 | 6/2015 | Kovalsky et al. |
| 9,072,604 B1 | 7/2015 | Melnick et al. |
| 9,084,676 B2 | 7/2015 | Chau et al. |
| 9,132,006 B2 | 9/2015 | Spenser et al. |
| 9,155,617 B2 | 10/2015 | Carpentier et al. |
| 9,168,130 B2 | 10/2015 | Straubinger |
| 9,168,133 B2 | 10/2015 | Spenser et al. |
| 9,173,738 B2 | 11/2015 | Murray, III et al. |

(56) References Cited

U.S. PATENT DOCUMENTS

| | | |
|---|---|---|
| 9,192,466 B2 | 11/2015 | Kovalsky et al. |
| 9,226,826 B2 | 1/2016 | Rust |
| 9,241,792 B2 | 1/2016 | Benichou et al. |
| 9,248,016 B2 | 2/2016 | Oba |
| 9,259,315 B2 | 2/2016 | Zhou et al. |
| 9,265,631 B2 | 2/2016 | Straubinger |
| 9,289,293 B2 | 3/2016 | Murad et al. |
| 9,295,547 B2 | 3/2016 | Costello et al. |
| 9,295,548 B2 | 3/2016 | Drews et al. |
| 9,295,550 B2 | 3/2016 | Nguyen et al. |
| 9,301,843 B2 | 4/2016 | Richardson et al. |
| 9,301,863 B2 | 4/2016 | Punga et al. |
| 9,331,328 B2 | 5/2016 | Eberhardt et al. |
| 9,339,377 B2 | 5/2016 | Quadri et al. |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,345,573 B2 | 5/2016 | Nyuli et al. |
| 9,358,111 B2 | 6/2016 | Spence et al. |
| 9,370,423 B2 | 6/2016 | Ryan |
| 9,370,424 B2 | 6/2016 | Call et al. |
| 9,375,311 B2 | 6/2016 | Gloss et al. |
| 9,439,757 B2 | 6/2016 | Wallace et al. |
| 9,492,273 B2 | 6/2016 | Wallace et al. |
| 9,387,071 B2 | 7/2016 | Tuval et al. |
| 9,402,719 B2 | 8/2016 | Lane et al. |
| 9,402,721 B2 | 8/2016 | Buchbinder et al. |
| 9,414,913 B2 | 8/2016 | Beith et al. |
| 9,414,918 B2 | 8/2016 | Chau et al. |
| 9,433,503 B2 | 9/2016 | Tsukashina et al. |
| 9,456,896 B2 | 10/2016 | Quadri et al. |
| 9,468,525 B2 | 10/2016 | Kovalsky |
| 9,480,556 B2 | 11/2016 | Revuelta et al. |
| 9,480,559 B2 | 11/2016 | Vidlund et al. |
| 9,486,306 B2 | 11/2016 | Tegels et al. |
| 9,510,946 B2 | 12/2016 | Chau et al. |
| 9,522,062 B2 | 12/2016 | Tuval |
| 9,532,870 B2 | 1/2017 | Cooper et al. |
| 9,554,903 B2 | 1/2017 | Rowe et al. |
| 9,561,100 B2 | 2/2017 | Pintor et al. |
| 9,561,103 B2 | 2/2017 | Granada et al. |
| 9,572,662 B2 | 2/2017 | Morriss et al. |
| 9,579,194 B2 | 2/2017 | Elizondo et al. |
| 9,579,196 B2 | 2/2017 | Morriss et al. |
| 2001/0007956 A1 | 7/2001 | Letac et al. |
| 2001/0021872 A1 | 9/2001 | Bailey et al. |
| 2002/0151970 A1 | 10/2002 | Garrison et al. |
| 2003/0055492 A1 | 3/2003 | Shaolian et al. |
| 2003/0130726 A1 | 7/2003 | Thorpe et al. |
| 2004/0127982 A1 | 7/2004 | Machold et al. |
| 2004/0210307 A1 | 10/2004 | Khairkhahan |
| 2004/0260393 A1 | 12/2004 | Randert et al. |
| 2005/0010287 A1 | 1/2005 | Macoviak et al. |
| 2005/0137689 A1 | 6/2005 | Salahieh et al. |
| 2005/0137690 A1 | 6/2005 | Salahieh et al. |
| 2005/0165479 A1 | 7/2005 | Drews et al. |
| 2005/0234546 A1* | 10/2005 | Nugent .............. A61F 2/2412 623/2.11 |
| 2006/0235509 A1 | 10/2006 | Lafontaine |
| 2007/0027533 A1 | 2/2007 | Douk |
| 2007/0168024 A1 | 7/2007 | Khairkhahan |
| 2008/0004697 A1 | 1/2008 | Lichetenstein et al. |
| 2008/0015671 A1 | 1/2008 | Bonhoeffer |
| 2008/0086164 A1 | 4/2008 | Rowe |
| 2008/0103586 A1 | 5/2008 | Styrc et al. |
| 2008/0140189 A1 | 6/2008 | Nguyen et al. |
| 2008/0208327 A1 | 8/2008 | Rowe |
| 2008/0221672 A1 | 9/2008 | Lamphere et al. |
| 2009/0005863 A1 | 1/2009 | Goetz et al. |
| 2009/0112309 A1* | 4/2009 | Jaramillo .............. A61F 2/2412 623/1.26 |
| 2009/0216312 A1 | 8/2009 | Straubinger et al. |
| 2010/0049315 A1 | 2/2010 | Kirson |
| 2010/0100173 A1 | 4/2010 | Lafontaine |
| 2010/0145440 A1 | 6/2010 | Keranen |
| 2010/0217382 A1 | 8/2010 | Chau et al. |
| 2010/0249894 A1 | 9/2010 | Oba |
| 2010/0249908 A1 | 9/2010 | Chau et al. |
| 2010/0262232 A1 | 10/2010 | Annest |
| 2010/0280606 A1 | 11/2010 | Naor |
| 2010/0298931 A1* | 11/2010 | Quadri .............. A61F 2/2418 623/2.11 |
| 2010/0312333 A1 | 12/2010 | Navia et al. |
| 2010/0331972 A1 | 12/2010 | Pintor et al. |
| 2011/0004296 A1 | 1/2011 | Lutter et al. |
| 2011/0022168 A1 | 1/2011 | Cartledge |
| 2011/0040374 A1 | 2/2011 | Goetz et al. |
| 2011/0137397 A1 | 6/2011 | Chau et al. |
| 2011/0137410 A1 | 6/2011 | Hacohen |
| 2011/0166636 A1 | 7/2011 | Rowe |
| 2011/0208293 A1 | 8/2011 | Tabor |
| 2011/0208298 A1* | 8/2011 | Tuval .............. A61F 2/2418 623/2.17 |
| 2011/0218619 A1 | 9/2011 | Benichou et al. |
| 2011/0224785 A1 | 9/2011 | Hacohen |
| 2011/0245911 A1 | 10/2011 | Quill et al. |
| 2011/0257721 A1 | 10/2011 | Tabor |
| 2011/0282438 A1 | 11/2011 | Drews et al. |
| 2011/0295363 A1 | 12/2011 | Girard et al. |
| 2011/0301688 A1 | 12/2011 | Rust et al. |
| 2011/0319988 A1 | 12/2011 | Schankereli et al. |
| 2011/0319989 A1* | 12/2011 | Lane .............. A61F 2/2418 623/2.11 |
| 2012/0010697 A1 | 1/2012 | Shin et al. |
| 2012/0016464 A1 | 1/2012 | Seguin |
| 2012/0035722 A1 | 2/2012 | Tuval |
| 2012/0053675 A1 | 3/2012 | Borock |
| 2012/0059458 A1 | 3/2012 | Buchbinder et al. |
| 2012/0078357 A1 | 3/2012 | Conklin |
| 2012/0101571 A1 | 4/2012 | Thambar et al. |
| 2012/0136430 A1 | 5/2012 | Sochman et al. |
| 2012/0165930 A1 | 6/2012 | Gifford, III et al. |
| 2012/0310328 A1 | 12/2012 | Olson et al. |
| 2013/0053949 A1 | 2/2013 | Pintor et al. |
| 2013/0079869 A1 | 3/2013 | Straubinger |
| 2013/0090725 A1 | 4/2013 | Pintor et al. |
| 2013/0116777 A1 | 5/2013 | Pintor et al. |
| 2013/0172978 A1* | 7/2013 | Vidlund .............. A61B 17/0401 623/1.12 |
| 2013/0172992 A1 | 7/2013 | Gross et al. |
| 2013/0184811 A1 | 7/2013 | Rowe et al. |
| 2013/0211508 A1* | 8/2013 | Lane .............. A61F 2/2403 623/2.11 |
| 2013/0282110 A1 | 10/2013 | Schweich et al. |
| 2013/0282114 A1 | 10/2013 | Schweich et al. |
| 2013/0304200 A1 | 11/2013 | McLean et al. |
| 2013/0310928 A1* | 11/2013 | Morriss .............. A61F 2/2418 623/2.12 |
| 2013/0345799 A1 | 12/2013 | Lafontaine |
| 2014/0005778 A1 | 1/2014 | Buchbinder et al. |
| 2014/0012368 A1* | 1/2014 | Sugimoto .............. A61L 31/022 623/2.11 |
| 2014/0012372 A1 | 1/2014 | Chau et al. |
| 2014/0012373 A1 | 1/2014 | Chau et al. |
| 2014/0039611 A1 | 2/2014 | Lane et al. |
| 2014/0052237 A1 | 2/2014 | Lane et al. |
| 2014/0200662 A1 | 7/2014 | Eftel et al. |
| 2014/0214156 A1 | 7/2014 | Navia et al. |
| 2014/0222136 A1 | 8/2014 | Geist et al. |
| 2014/0228946 A1 | 8/2014 | Chau et al. |
| 2014/0236291 A1 | 8/2014 | Schweich et al. |
| 2014/0257467 A1 | 9/2014 | Lane et al. |
| 2014/0316516 A1* | 10/2014 | Vidlund .............. A61F 2/2418 623/2.1 |
| 2014/0343669 A1 | 11/2014 | Lane et al. |
| 2014/0358223 A1 | 12/2014 | Rafiee et al. |
| 2014/0364943 A1 | 12/2014 | Conklin |
| 2015/0039083 A1 | 2/2015 | Rafiee |
| 2015/0094802 A1 | 4/2015 | Buchbinder et al. |
| 2015/0112433 A1 | 4/2015 | Schweich et al. |
| 2015/0127096 A1 | 5/2015 | Rowe et al. |

(56) References Cited

U.S. PATENT DOCUMENTS

| | | | |
|---|---|---|---|
| 2015/0142103 A1* | 5/2015 | Vidlund | A61F 2/2418 623/2.17 |
| 2015/0150678 A1 | 6/2015 | Brecker | |
| 2015/0157458 A1 | 6/2015 | Thambar et al. | |
| 2015/0173897 A1 | 6/2015 | Raanani et al. | |
| 2015/0196390 A1 | 7/2015 | Ma et al. | |
| 2015/0216656 A1 | 8/2015 | Pintor et al. | |
| 2015/0216657 A1 | 8/2015 | Braido | |
| 2015/0216660 A1 | 8/2015 | Pintor et al. | |
| 2015/0238312 A1 | 8/2015 | Lashinski | |
| 2015/0238313 A1 | 8/2015 | Spence et al. | |
| 2015/0265402 A1 | 9/2015 | Centola et al. | |
| 2015/0320553 A1 | 11/2015 | Chau et al. | |
| 2015/0327995 A1 | 11/2015 | Morin et al. | |
| 2015/0327996 A1 | 11/2015 | Fahim et al. | |
| 2015/0327999 A1 | 11/2015 | Board et al. | |
| 2015/0335421 A1 | 11/2015 | Figulla et al. | |
| 2015/0342733 A1 | 12/2015 | Alkhatib et al. | |
| 2015/0351906 A1 | 12/2015 | Hammer et al. | |
| 2015/0359629 A1 | 12/2015 | Ganesan et al. | |
| 2016/0000564 A1 | 1/2016 | Buchbinder et al. | |
| 2016/0008131 A1 | 1/2016 | Christianson et al. | |
| 2016/0022417 A1 | 1/2016 | Karapetian et al. | |
| 2016/0045307 A1 | 2/2016 | Yohanan et al. | |
| 2016/0045309 A1 | 2/2016 | Valdez et al. | |
| 2016/0051362 A1 | 2/2016 | Cooper et al. | |
| 2016/0074160 A1 | 3/2016 | Christianson et al. | |
| 2016/0106539 A1 | 4/2016 | Buchbinder et al. | |
| 2016/0120646 A1 | 5/2016 | Dwork et al. | |
| 2016/0158000 A1 | 6/2016 | Granada et al. | |
| 2016/0158001 A1 | 6/2016 | Wallace et al. | |
| 2016/0158003 A1 | 6/2016 | Wallce et al. | |
| 2016/0184095 A1 | 6/2016 | Spence et al. | |
| 2016/0193044 A1 | 7/2016 | Achiluzzi | |
| 2016/0199180 A1 | 7/2016 | Zeng et al. | |
| 2016/0220364 A1 | 8/2016 | Straubinger | |
| 2016/0228251 A1 | 8/2016 | Nyuli et al. | |
| 2016/0235529 A1 | 8/2016 | Ma et al. | |
| 2016/0242906 A1 | 8/2016 | Morriss et al. | |
| 2016/0270917 A1 | 9/2016 | Tuval et al. | |
| 2016/0310268 A1 | 10/2016 | Oba et al. | |
| 2016/0317290 A1 | 11/2016 | Chau et al. | |
| 2016/0317304 A1 | 11/2016 | Spence et al. | |
| 2016/0324631 A1 | 11/2016 | Lane et al. | |
| 2016/0324633 A1 | 11/2016 | Gross et al. | |
| 2016/0331523 A1 | 11/2016 | Chau et al. | |
| 2016/0331531 A1 | 11/2016 | Quadri et al. | |
| 2016/0331534 A1 | 11/2016 | Buchbinder et al. | |
| 2016/0338826 A1 | 11/2016 | Chau et al. | |
| 2016/0338829 A1 | 11/2016 | Call et al. | |
| 2016/0346080 A1 | 12/2016 | Righini et al. | |
| 2016/0354203 A1 | 12/2016 | Tuval et al. | |
| 2016/0354204 A1 | 12/2016 | Braido et al. | |
| 2016/0361162 A1 | 12/2016 | Richter et al. | |
| 2016/0361163 A1 | 12/2016 | Yohanan et al. | |
| 2016/0374801 A1 | 12/2016 | Jiminez et al. | |
| 2017/0007398 A1 | 1/2017 | Drews et al. | |
| 2017/0049564 A1 | 2/2017 | Board et al. | |
| 2017/0056162 A1 | 3/2017 | Harewood | |
| 2017/0056163 A1 | 3/2017 | Tayeb et al. | |
| 2017/0056166 A1 | 3/2017 | Ratz et al. | |
| 2017/0056176 A1 | 3/2017 | Rowe et al. | |

FOREIGN PATENT DOCUMENTS

| | | |
|---|---|---|
| EP | 592410 | 4/1994 |
| EP | 705081 | 10/2001 |
| EP | 1338255 | 8/2003 |
| EP | 825841 | 10/2003 |
| EP | 833595 | 10/2003 |
| EP | 910313 | 11/2003 |
| EP | 910314 | 11/2003 |
| EP | 0910314 | 11/2003 |
| EP | 1006949 | 10/2004 |
| EP | 1233731 | 12/2004 |
| EP | 1251803 | 6/2005 |
| EP | 2674130 | 6/2005 |
| EP | 1267753 | 10/2005 |
| EP | 830112 | 11/2005 |
| EP | 1171059 | 11/2005 |
| EP | 1328215 | 11/2005 |
| EP | 1318775 | 11/2006 |
| EP | 1474077 | 2/2007 |
| EP | 1143882 | 12/2007 |
| EP | 1180987 | 8/2008 |
| EP | 1237509 | 12/2008 |
| EP | 1562522 | 12/2008 |
| EP | 2000115 | 12/2008 |
| EP | 1330213 | 3/2009 |
| EP | 1610727 | 4/2009 |
| EP | 1343438 | 7/2009 |
| EP | 2078498 | 7/2009 |
| EP | 1684667 | 8/2009 |
| EP | 1408850 | 9/2009 |
| EP | 1653888 | 9/2009 |
| EP | 1049425 | 11/2009 |
| EP | 1703865 | 2/2010 |
| EP | 1682048 | 3/2010 |
| EP | 1509171 | 6/2010 |
| EP | 1968491 | 7/2010 |
| EP | 1176913 | 10/2010 |
| EP | 1465554 | 12/2010 |
| EP | 1940321 | 12/2010 |
| EP | 2255312 | 12/2010 |
| EP | 1441672 | 9/2011 |
| EP | 2160150 | 10/2011 |
| EP | 1603493 | 12/2011 |
| EP | 2399549 | 12/2011 |
| EP | 2399550 | 12/2011 |
| EP | 1788984 | 2/2012 |
| EP | 2055266 | 2/2012 |
| EP | 2420205 | 2/2012 |
| EP | 1621162 | 5/2012 |
| EP | 2138132 | 6/2012 |
| EP | 2476394 | 7/2012 |
| EP | 2124824 | 10/2012 |
| EP | 2088965 | 11/2012 |
| EP | 2526895 | 11/2012 |
| EP | 2526898 | 11/2012 |
| EP | 2526899 | 11/2012 |
| EP | 2529696 | 12/2012 |
| EP | 2529697 | 12/2012 |
| EP | 2529698 | 12/2012 |
| EP | 2529699 | 12/2012 |
| EP | 2537487 | 12/2012 |
| EP | 1919397 | 1/2013 |
| EP | 2015709 | 1/2013 |
| EP | 1750622 | 2/2013 |
| EP | 2257242 | 2/2013 |
| EP | 2260796 | 2/2013 |
| EP | 1701668 | 3/2013 |
| EP | 2260797 | 3/2013 |
| EP | 2340075 | 3/2013 |
| EP | 2260798 | 6/2013 |
| EP | 2626040 | 8/2013 |
| EP | 1758523 | 9/2013 |
| EP | 2073756 | 10/2013 |
| EP | 2109417 | 11/2013 |
| EP | 2477555 | 12/2013 |
| EP | 1838241 | 2/2014 |
| EP | 1926455 | 4/2014 |
| EP | 2405966 | 4/2014 |
| EP | 2257243 | 5/2014 |
| EP | 2316381 | 5/2014 |
| EP | 2745805 | 6/2014 |
| EP | 2117469 | 7/2014 |
| EP | 2124826 | 7/2014 |
| EP | 2258316 | 7/2014 |
| EP | 2749254 | 7/2014 |
| EP | 1667604 | 8/2014 |
| EP | 2211779 | 8/2014 |
| EP | 2772228 | 9/2014 |
| EP | 2142143 | 11/2014 |

(56) References Cited

FOREIGN PATENT DOCUMENTS

| | | |
|---|---|---|
| EP | 2815723 | 12/2014 |
| EP | 2815724 | 12/2014 |
| EP | 2815725 | 12/2014 |
| EP | 2254515 | 1/2015 |
| EP | 1465555 | 5/2015 |
| EP | 2068767 | 7/2015 |
| EP | 1702247 | 8/2015 |
| EP | 1729688 | 8/2015 |
| EP | 2262447 | 8/2015 |
| EP | 2901966 | 8/2015 |
| EP | 1804686 | 9/2015 |
| EP | 2675396 | 9/2015 |
| EP | 1734903 | 10/2015 |
| EP | 2254513 | 10/2015 |
| EP | 2544626 | 10/2015 |
| EP | 2926766 | 10/2015 |
| EP | 2926767 | 10/2015 |
| EP | 1748745 | 12/2015 |
| EP | 1755459 | 12/2015 |
| EP | 1850796 | 12/2015 |
| EP | 1991168 | 1/2016 |
| EP | 2254512 | 1/2016 |
| EP | 2263609 | 1/2016 |
| EP | 2012712 | 2/2016 |
| EP | 1585463 | 3/2016 |
| EP | 2170416 | 3/2016 |
| EP | 2278944 | 3/2016 |
| EP | 1871300 | 4/2016 |
| EP | 2572676 | 4/2016 |
| EP | 2626041 | 4/2016 |
| EP | 2237746 | 5/2016 |
| EP | 2582326 | 5/2016 |
| EP | 2618784 | 5/2016 |
| EP | 1734902 | 6/2016 |
| EP | 1906884 | 6/2016 |
| EP | 2190379 | 6/2016 |
| EP | 2416739 | 6/2016 |
| EP | 2572675 | 6/2016 |
| WO | WO 2011/119101 | 9/2011 |
| WO | WO 2012/103204 | 8/2012 |
| WO | WO 2015/061463 | 4/2015 |

OTHER PUBLICATIONS

Supplementary European Search Report in Eurpoean Application No. 13778768, dated Jan. 12, 2016, 7 pages.
International Search Report and Written Opinion in International Application No. PCT/US2015/056935, dated Feb. 12, 2016, 14 pages.
U.S. Appl. No. 61/266,774, filed Dec. 16, 2009, Chau et al.
U.S. Appl. No. 61/287,099, filed Dec. 4, 2009, Chau et al.
International Preliminary Report on Patentability in International Application No. PCT/US2015/035303, dated Dec. 15, 2016, 10 pages.
European Search Report in European Application No. 15807060.7, dated Jun. 6, 2017, 7 pages.
International Search Report and Written Opinion in International Application No. PCT/US2016/069201, dated Apr. 28, 2017, 12 pages.

* cited by examiner

TWO STAGE ANCHOR AND MITRAL VALVE ASSEMBLY

CROSS REFERENCE TO RELATED APPLICATIONS

This application claims the benefit of U.S. Application Ser. No. 62/011,164, filed Jun. 12, 2014. The disclosure of the prior application is considered part of and is incorporated by reference in the disclosure of this application.

BACKGROUND OF THE DISCLOSURE

The present disclosure relates to heart valve interventional systems and methods and more particularly, to mitral valve therapy systems and methods.

The long-term clinical effect of valve regurgitation is well recognized as a significant contributor to cardiovascular related morbidity and mortality. Thus, the primary goal of any therapy of the mitral valve is to significantly reduce or eliminate the regurgitation. By eliminating the regurgitation, the destructive volume overload effects on the left ventricle are attenuated. The volume overload of mitral regurgitation (MR) relates to the excessive kinetic energy required during isotonic contraction to generate overall stroke volume in an attempt to maintain forward stroke volume and cardiac output. It also relates to the pressure potential energy dissipation of the leaking valve during the most energy-consuming portion of the cardiac cycle, isovolumic contraction. Additionally, successful MR reduction should have the effect of reducing the elevated pressures in the left atrium and pulmonary vasculature reducing pulmonary edema (congestion) and shortness of breath symptomatology. It also has a positive effect on the filling profile of the left ventricle (LV) and the restrictive LV physiology that can result with MR. These pathophysiologic issues indicate the potential benefits of MR therapy, but also indicates the complexity of the system and the need for a therapy to focus beyond the MR level or grade.

It is also desirable to prevent new deleterious physiology or function of the valve. The procedure and system used to fix the mitral valve ideally should avoid worsening other (non-MR) existing pathologic conditions or creating new pathologic conditions as a result of the treatment. One of the critical factors to be managed is mitral stenosis or creation of an inflow gradient. That is, if a valve system is used that does not allow for sufficient LV inflow without elevated filling pressures, then critical benefits of MR reduction are dissipated or lost. Moreover, atrial fibrillation is to be avoided as it can result if elevated pressures are not relieved by the therapy, or are created by the system (high pressure results in atrial stress leading to dilatation ultimately leading to arrhythmias). Also, if the procedure results in damage to atrial tissue at surgery, it can result in the negative physiologic effect of atrial fibrillation. Further, one should be aware of the possibility of increased LV wall stress through an increase in LV size (LV geometry). Due to the integral relationship of the mitral valve with LV geometry through the papillary and chordal apparatus, LV wall stress levels can be directly affected resulting in alterations of LV filling and contraction mechanics. Accordingly, a system that does not preserve or worsens the geometry of the LV can counter the benefits of MR reduction because of the alteration of contractile physiology.

It has been generally agreed that it is preferable if the native valve can be repaired (e.g. with an annular ring), versus an open surgical valve replacement. Repair of valve elements that target the regurgitant jet only results in minimal alteration to the valve elements/structures that are properly functioning allowing for the least potential for negatively affecting the overall physiology while achieving the primary goal. Native valve preservation can be beneficial because a well repaired valve is considered to have a better chance of having long standing durability versus a replacement with an artificial valve that has durability limits. Also, while current surgical artificial valves attempt chord sparing procedures, the LV geometric relationship may be negatively altered if not performed or performed poorly leading to an increase in LV wall stress due to an increase in LV diameter. Thus, while repair is preferred and possible for technically competent surgeons, the relatively high recurrence rate of MR due to inadequate repair, the invasiveness of the surgery especially in sick or functional MR patients, and the complexities of a repair for many surgeons lead to a high percentage of mitral operations being surgical replacement.

Conventionally, surgical repair or replacement of the mitral valve is performed on cardiopulmonary bypass and is usually performed via an open median sternotomy resulting in one of the most invasive high risk cardiac surgical operations performed, especially in subpopulations such as those with functional MR. Therefore, a key improvement to mitral valve operations is to significantly lower the risk and invasiveness, specifically utilizing a percutaneous or minimally invasive technique.

While there have been attempts to replicate existing surgical repair via less invasive surgical or percutaneous methods, given the complexity of repairing the valve surgically, the efforts have largely been deemed lacking in achieving adequate efficacy and have not altered the risk benefit ratio sufficiently to warrant ongoing investment, regulatory approval, or adoption. In particular, there has been a general technology failure due to the complexity of anatomy to percutaneously manage with an implant or implantable procedure. The broad spectrum of mitral disease directly influences outcomes with a resulting inability to match technology with pathology. There has also been observed inadequate efficacy with poor surgical replication and safety results. It has also been recognized that percutaneous approaches have been successful to certain valve procedures, such as aortic valve replacement associated with a single pathology and a relatively circular rigid substrate, mitral valves often suffer from multiple pathologies and a have flexible or elastic annulus with multiple structures, making this a more challenging goal.

Further challenges exist in positioning and orienting mitral regurgitation therapy structures at the interventional site. Cooperation and sealing between component parts has also been a consideration in effective mitral regurgitation therapy. Additionally, more can be done to both identify and take advantage of native anatomical features common to the mitral valve. More can also be done to streamline the implantation process.

Accordingly, what is needed is an effective long lasting MR reduction without creating negative physiologic consequences to the cardio-pulmonary system (heart, lungs, peripheral vasculature) including stenosis, LV wall stress and atrial fibrillation. It is also desirable to be able to perform the operation in a reliable, repeatable, and easy to perform procedure and to have a broadly applicable procedure for both patients and physicians, while employing a significantly less invasive method. Moreover, it is desirable to take advantage of anatomical features leading themselves to an effective mitral regurgitation therapy, and to provide component structures which cooperate to address regurgitation as well as implantation aids facilitating proper orientation and placement.

The present disclosure addresses these and other needs.

SUMMARY

Briefly and in general terms, the present disclosure is directed towards replacement systems and methods. In one particular aspect, the present disclosure describes a percutaneous or minimally invasive mitral valve replacement system that eliminates MR, provides adequate physiologic inflow, and preserves and/or improves LV geometry in a reliable, repeatable, and easy to perform procedure.

In one aspect, there is provided a mitral valve replacement system including an anchoring structure and an artificial valve configured to treat a native heart. The assembly can include one or more of anterior and posterior atrial stabilizers and a systolic anterior motion (SAM) stabilization feature. Moreover, an anchor assembly can be configured with four feet or projections sized and shaped to engage an anatomical gutter located in the left ventricle proximate the mitral valve annulus which acts as support for subsequent implantation of a replacement valve assembly. The anchor can further include valve retaining structure for positioning the valve supra-annularly. Such retaining structure can be ring-like including connected arches with webbing and intra-arch supports. Sealing with native valve structure is provided by a valve skirt. Device delivery control features can be provided on superior aspects of anchor arches. The anchor can also include a hub which can be manipulated for accomplishing delivery.

The anchor assembly includes structure for placement at or proximate a mitral valve annulus, as well as structure for sealing within anatomy and engagement of the mitral valve assembly. The implanted mitral valve presents a tri-leaflet structure for controlling blood flow, as well as structure for accomplishing a seal within the anchor. In certain approaches, forces can be translated to various anatomical features of and proximate the mitral valve. In one approach, an anchor assembly can be implanted within the anatomical gutter leaving the leaflets of the mitral valve unaffected in terms of valve function. In other approaches, structure of the anchor can cross the annulus of the mitral valve and can further partially or completely retain leaflets. Thus, forces generated by the heart and inherent in blood flow can be translated by an anchor directly and solely to the anatomical gutter, or such forces can be in part translated to leaflet, chordae and papillary muscle anatomy to varying degrees.

In one approach, the mitral valve replacement system addresses a number of basic functional requirements. One requirement is the valve function itself, the occlusion of flow during systole, and open to flow during diastole. Another requirement is the seal between the artificial replacement valve frame/structure and the tissue to prevent/minimize any paravalvular leaks or flow. A further requirement is the anchoring or securement function to hold the functioning valve in position and withstand the substantial and variable cyclical load placed on the valve during systolic pressurization of the valve surface. It is intended that each of these is met in the durable, therapeutically, and physiologically appropriate mitral valve replacement system disclosed herein.

The presently disclosed system may utilize a staged approach to the functional elements of the system, starting with the anchoring or securement functional element. Additionally, the staging can be performed within a single procedure or in multiple, time separated procedures, e.g. on different days. By staging and separating functional elements, the individual elements will be simpler in design and simpler to deploy and implant. This staging of the anchor implantation of the present invention provides a stable, reliable, consistent, substrate to deliver a replacement valve into the mitral position.

A mitral valve treatment system according to the present disclosure includes one or more of an anchor element, a sealing element, and a valve element, and can utilize an anchor delivery system, and a valve delivery system. More than one element may be incorporated into a structure, for example, an anchor element also may include a sealing structure, or a valve element may include a sealing structure. In accordance with the present teachings, the elements of the valve replacement system may be implanted in staged procedures, for example, an anchor element may be implanted during a first procedure and a valve element may be implanted during a second procedure. As disclosed herein, the processes, systems used for implantation, and timing of implantation may vary. The present disclosure further contemplates that the anchor element (and in some cases sealing element) of the disclosed mitral valve replacement system may be used with existing valve technologies, as discussed further below. Similarly, delivery systems may include those disclosed herein, but the present disclosure also contemplates that existing delivery systems may be used to deliver prior art valve structures.

Moreover, the valve anchor approach can fundamentally alter the complexity of performing a completely percutaneous mitral replacement by creating a reliable and consistent substrate. Thus, it is intended that the implant design make use of the geometry/mechanics of the commissures to create sufficient holding capability. In one particular aspect, as stated, the anatomical gutter found below a valve annulus is the site for anchoring. Further, design and delivery approaches that maintain native valve function providing the ability to completely separate and stage the implantation of the system functional components is contemplated as are delivery methods that have potential for quick fluoroscopic delivery, positioning, and deployment. Consequently, there is an optimal valve performance opportunity due to maximal design flexibility and technology leveraging, and a delivery capability to achieve precise positioning prior to valve deployment. The same creates desired tissue/implant sealing and maintains sub-valvular structural relationships.

Accordingly, employing the present system and method facilitates effective long lasting MR reduction without creating negative physiologic consequences to the cardio-pulmonary system (heart, lungs, peripheral vasculature) including stenosis, LV wall stress, and atrial fibrillation. The method can involve performance of the operation in a reliable, repeatable, and easy to perform procedure and is a broadly applicable procedure for both patients and physicians. A significantly less invasive method results, one which can be fully percutaneous from the start.

Other features and advantages of the present disclosure will become apparent from the following detailed description, taken in conjunction with the accompanying drawings, which illustrate, by way of example, the principles of the invention.

DETAILED DESCRIPTION OF THE PREFERRED EMBODIMENTS

Figure 1:
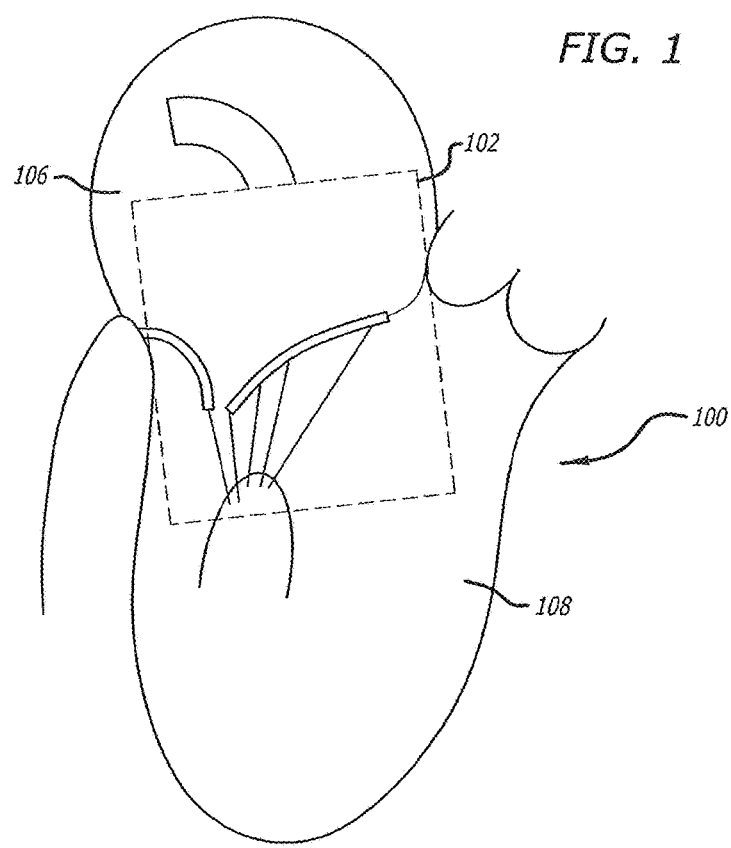
FIG. 1 is a cross-sectional view, depicting a native heart indicating an operating window region.

Referring now to the drawings, which are provided by way of background and example, and not limitation, the present disclosure relates to medical interventional procedures and devices. In various aspects, heart valve therapy is addressed and in particular, mitral valve replacement approaches are presented.

Overall, the present disclosure describes a system including an anchor, valve, and delivery technology that allows therapeutic flexibility (mitral replacement with either tissue or mechanical valves), implantation flexibility via either fully percutaneous or minimally invasive (trans-apical, trans-atrial) procedures, minimized delivery complexity to allow a simple to-perform procedure, and a patient population that is not restricted by the underlying pathology.

A mitral valve replacement system according to the present disclosure includes one or more of an anchor element, sealing structure, a valve element, and a valve delivery system. An anatomical gutter proximate the mitral valve is intended to be a target for anchoring at least portions of the replacement system. Generally, the gutter is a three dimensional composite LV sided anatomic structure that extends in a u-shape from one trigone region to the other bounded by the mitral leaflets on one side, annulus in the base region of the gutter, and the LV wall on the other side. Functionally, it collects and diverts sub-annular/leaflet blood during systole into the aortic outflow tract.

More than one element may be incorporated into a structure, for example, an anchor element also may include a sealing structure, or a valve element may include a sealing structure. In accordance with the present teachings, the elements of the valve replacement system may be implanted in staged procedures, for example, an anchor element may be implanted during a first procedure and a valve element may be implanted during a second procedure. As disclosed herein, the processes, systems used for implantation, and timing of implantation may vary. The present disclosure further contemplates that the anchor element (and in some cases sealing element) of the disclosed mitral valve replacement system may be used with existing valve structures, as discussed further below. Similarly, delivery systems may include those disclosed herein, but the present disclosure also contemplates that existing delivery systems may be used to deliver prior art valve structures.

It should be noted that in planned percutaneous structural heart interventions (TAVI, mitral repair, mitral replacement), there are typically at least two procedures performed for each individual patient. The first procedure includes a diagnostic assessment and possible PCI/stenting of the patient's coronary arteries and often includes a right heart cath for cardiac physiology assessment. Valve implantation and or repair are generally not performed prior to knowing the patient has been previously completely revascularized if necessary.

Generally the most difficult and most significant requirement for a less invasive valve system is the anchoring attachment of the system. The presently disclosed mitral valve replacement system staging of the anchor implantation allows the use of various anatomic valve and ventricular structures to achieve the required holding force of the anchor system. When performed in two time separated procedures, staging the implantation of the anchor separately from other system elements provides time for tissue ingrowth into the anchor structure and resultant strengthening of the overall holding force of the anchor structure in the anatomy.

Staging of anchor implantation allows for maintaining native valve function until artificial valve element(s) are in place. Staging also helps in mitral valve replacement where there is limited operating space. It is to be recognized that immediate valve placement after anchor implanting is contemplated.

With reference to FIG. 1, there is shown a schematic cross-section of a heart 100. A box 102 is provided to indicate an operating window for mitral valve replacement.

As can be gleaned from the schematic representation, the operating space for mitral valve replacement is limited by the size of the left atrium 106. Whereas the left ventricle 108 defines a larger space, when a repair procedure employs a left atrium approach, the cavity defined by the size of the left atrium 106 must be taken into consideration. Moreover, replacement structure and delivery systems must be sized and configured to be passed within and through, as well as function within the left atrium 106. In fact, the distance from a mitral valve annulus to a roof of the left atrium 106 is up to or approximately 4.5 cm. A delivery approach that delivers individual components separately (whether staged in separate procedures or not) can thus be advantageous since smaller sub-component parts can be introduced at the interventional site and later assembled. To wit, a fully assembled replacement device could be much more difficult to advance to the interventional site and be oriented properly to effect a replacement.

It is contemplated that anchor element embodiments utilize and exploit anatomic structures and geometry to attain the required mechanical holding forces whether engaged acutely or chronically with the addition of tissue ingrowth of the anchor. Another aspect is consideration of the anchor implant is the load distribution or force per unit of area of anchor attachment. This can be at a level that does not allow the anchor structure(s) to pull out of the tissue once attached. To maximize acute mechanical hold in the tissue, the profile geometry of the anchor tissue element can be designed to maximize the breadth and depth of tissue engagement as well as the surface width and geometry of the penetrating element. The tissue providing the holding force for the anchor can be used such that certain regions of the mitral valve have greater intrinsic tensile strength (e.g. anatomical gutter or trigone region) or utilize tissue that has a response that enhances the extent (thickness, area) of ingrowth (e.g. LV muscle wall). The tissue collagen orientation in certain regions needs to be accounted for if it is small chain, non-oriented fibers or can be used to maximize hold if it is larger chain and oriented collagen.

Due to the continuous and cyclical loads and motion of the system, anchor device mechanical integrity is likely required, specifically fatigue resistance, corrosion resistance and overall mechanical durability. One of the system elements is intended to interface with tissue to form a seal. This can be the anchor forming the seal and the valve seals to the anchor, or the anchor holds valve and a valve element seals to the tissue. The implanted valve interface to anchor can provide sufficient and stable holding capability with a transfer of the valve load effectively onto the anchor. This may be accomplished by a frictional fit via expansion of the valve into the anchor and/or tissue or a mechanical interlock mechanism between the anchor and valve. Further, the anchor implant structure can be a biocompatible device, including specific biocompatibility for blood contact and tissue contact.

The specific anatomic locations that may provide mechanical and structural attachment of the anchor is another area of consideration. The anchor may be designed to incorporate one or more of a commissural location such as the anterior trigone region or the posterior leaflet cleft. An attachment location could also be the anterior portion of an atrial wall, or at an annular region/surface (posterior or anterior). Leaflet capture is also contemplated such as at the sub-posterior leaflet or the sub commissural leaflet. Attachment can also be at or within the left ventricle (endocardial) such as to the posterior wall (including posterior leaflet capture or a papillary space wedge), the apical/sub-papillary, the anterior/posterior wall bridge, or transmurally (septal, free wall, apex).

Figure 2:
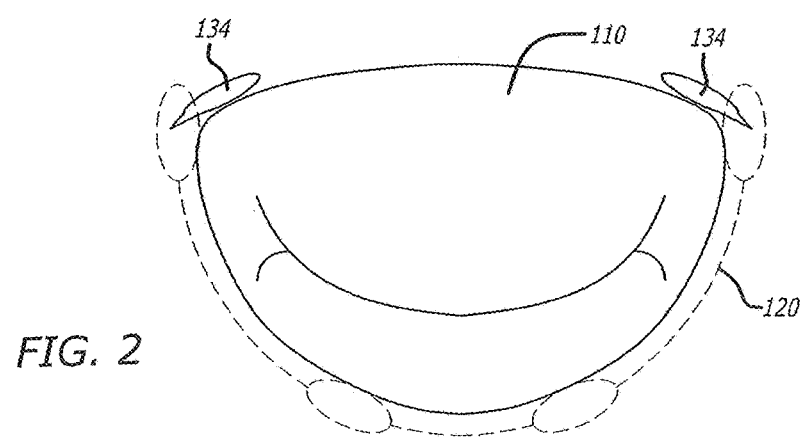
FIG. 2 is a top view, depicting a gutter perimeter of a valve including identified anchor locations.
Figure 3:
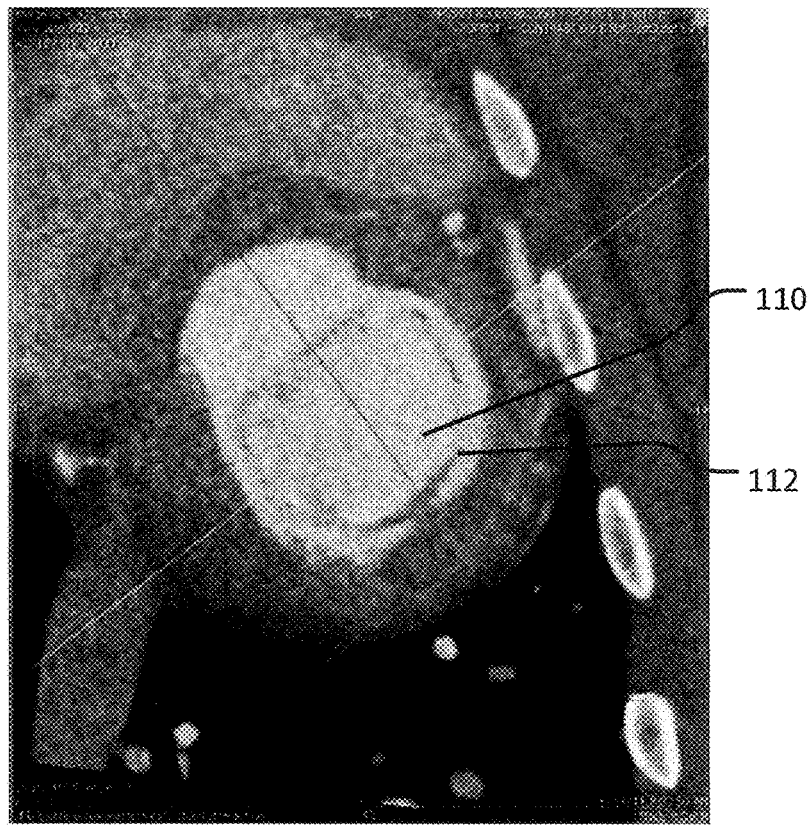
FIG. 3 is a CT sectional view of gutter anatomy, depicting leaflets and left ventricle wall with anchor locations identified.
Figure 4:
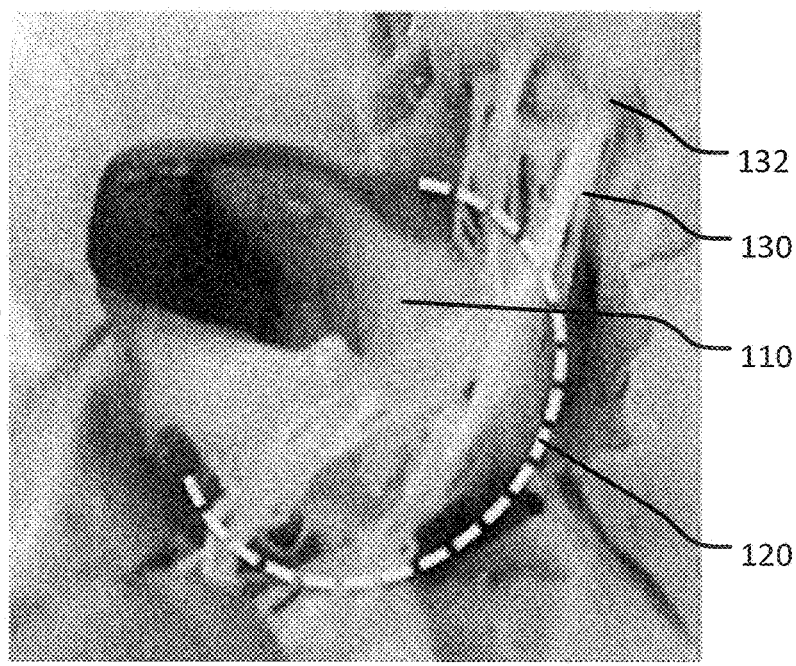
FIG. 4 is a sub-valvular view, depicting an anatomical gutter perimeter with anchor locations identified.

With reference to FIGS. 2-4, anatomical anchoring interface structure is presented. FIGS. 2-4 depict various views of a mitral valve 110. FIG. 2 depicts a top view of a closed mitral valve 110, the dashed line representing the anatomical location of a gutter 120 which provides stable and reliable anatomy for anchoring a mitral replacement device. The dashed ovals represent intended locations for anchor structure engagement. The arrows included in FIG. 3 point to the left ventricle wall in a schematic representation of a CT scan cross-sectional view to provide a sense of the anatomy defining the gutter 120 between the left ventricle wall and a leaflet edge 112. FIG. 4 provides a sub-valvular view of the mitral valve 110 to provide further details of relevant anatomy. A dashed line again depicts the location of the gutter 120, the arrows pointing to anchor structure engagement location. It is to be recognized that the complex anatomy of the native chordae 130 and papillary muscles 132 present challenges for anchor engagement. However, there is a consistent and predictable anatomical structure pattern which exists across patient populations. Thus, anchor engagement locations within the gutter 120 are chosen to avoid chordae 130 such that anchor feet or projection are configured to be placed within defined spaces between chordae and hook into engagement with the gutter 120 for sub-leaflet attachment. The gutter 120 advantageously presents muscle tissue having good ingrowth characteristics lending to enhancing anchor function. The gutter 120 also presents a space removed from leaflet function so there is little to no impact on native heart valve operation subsequent to the anchor placements. The fibrous trigone 134 (See FIG. 2) additionally provides a high collagen, structure element for acute anchoring.

Figure 5:
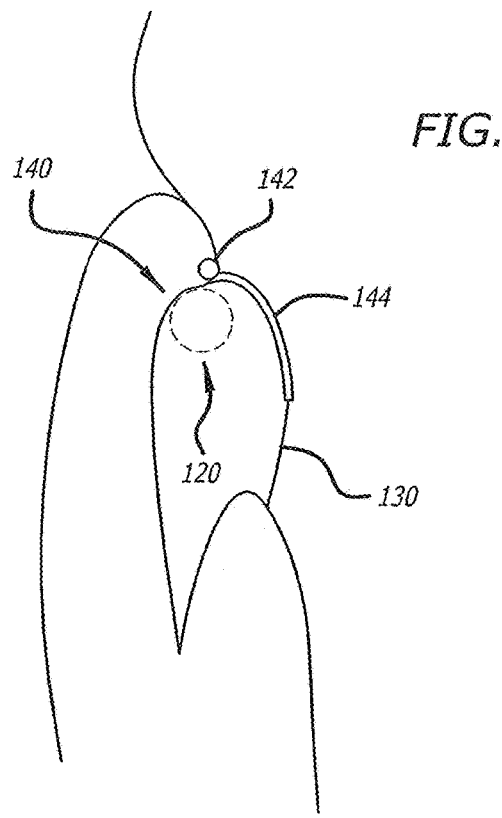
FIG. 5 is a side cross-sectional view, depicting tissue interfaces and an anatomical gutter with a leaflet closed.
Figure 6:
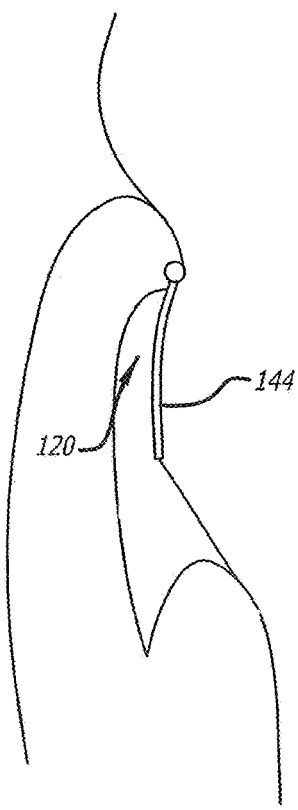
FIG. 6 is a side cross-sectional view, depicting tissue interfaces and anatomical gutter with a leaflet open.
Figure 7:
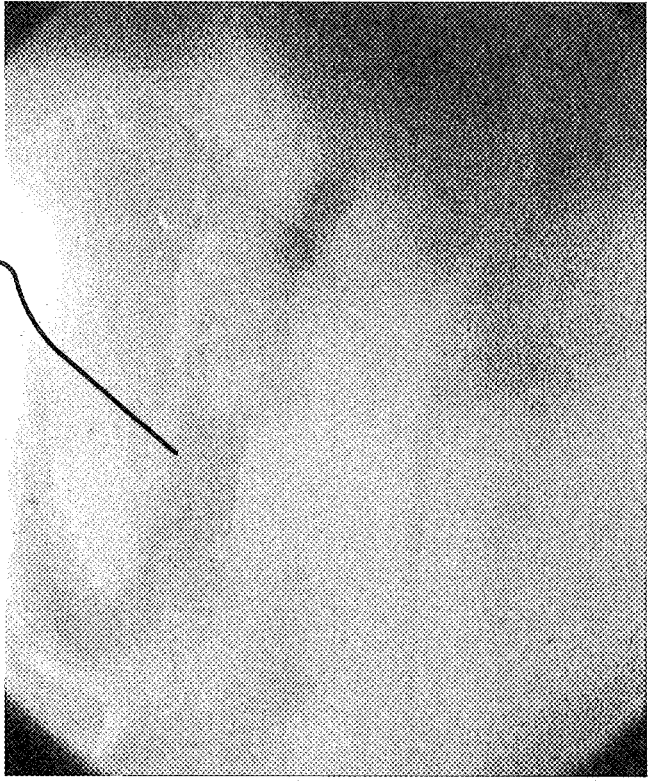
FIG. 7 is a lateral view, depicting a leaflet, subanular area behind the leaflet and a chordal web.
Figure 8:
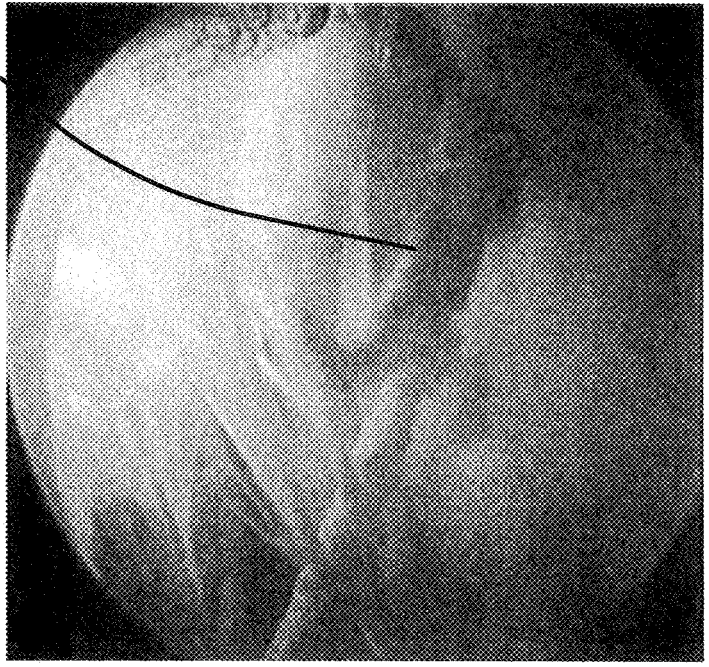
FIG. 8 is a rotated view, depicting an anchor foot passing through anatomy.
Figure 9:
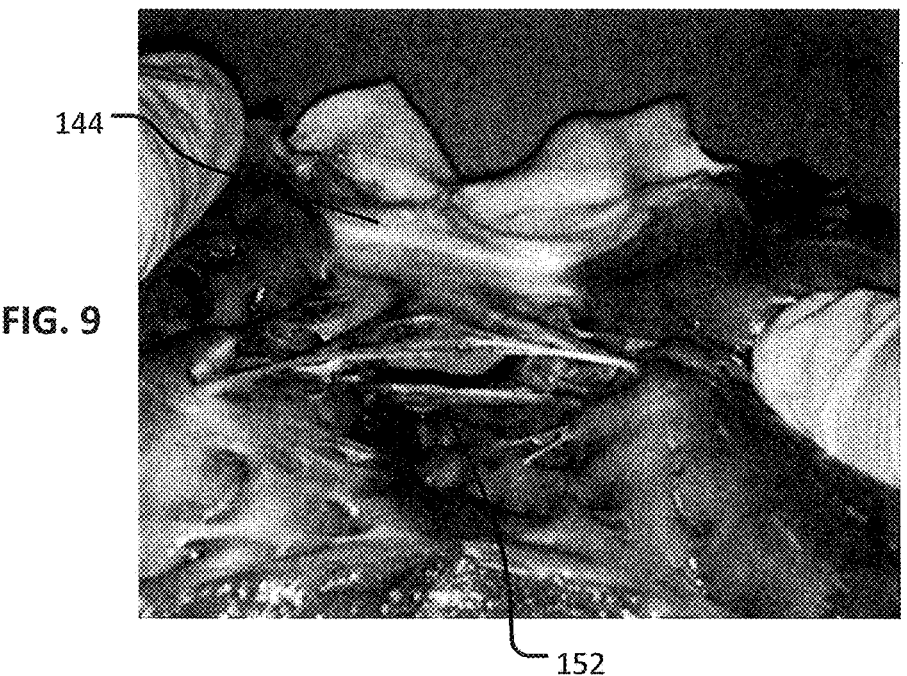
FIG. 9 is a perspective view, depicting a chordal tent with planar separation.
Figure 10:
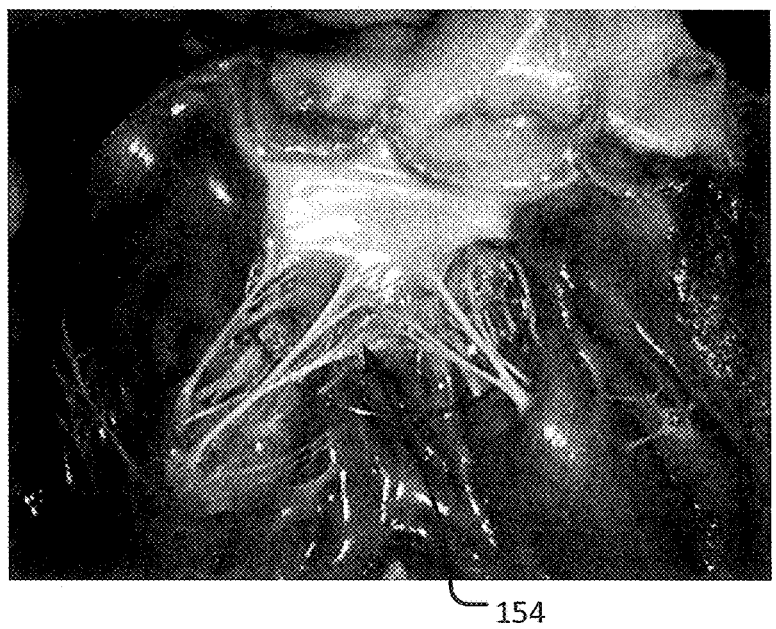
FIG. 10 is a perspective view, depicting loop structure passing through a coaptive margin.
Figure 11A:
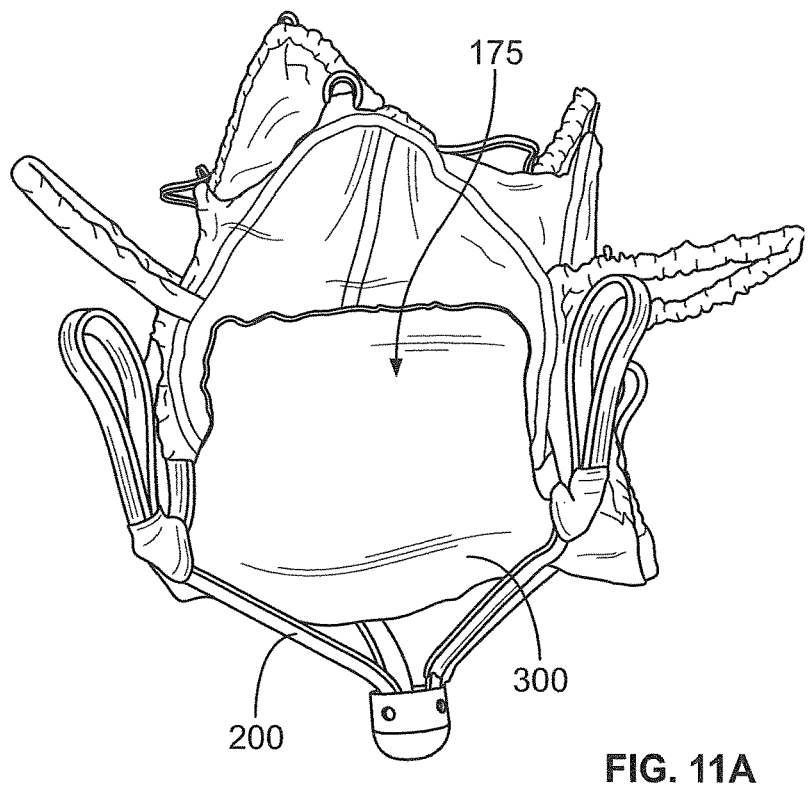
FIGS. 11A-D depict various views of an anchor and valve assembly.
Figure 11B:
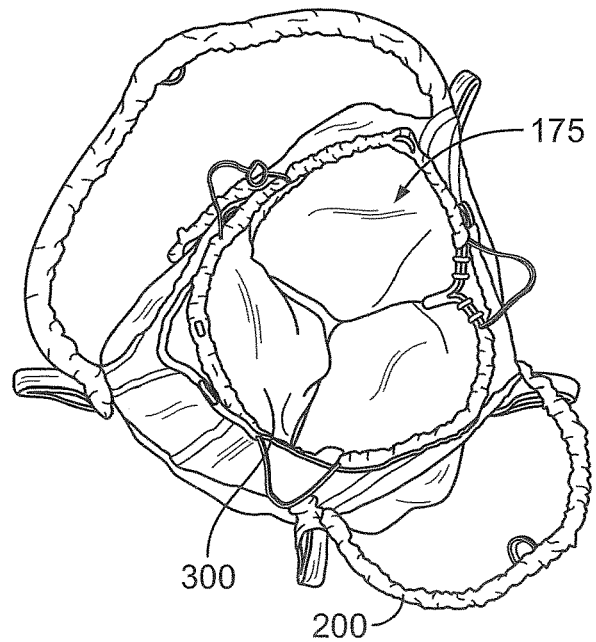
Figure 11C:
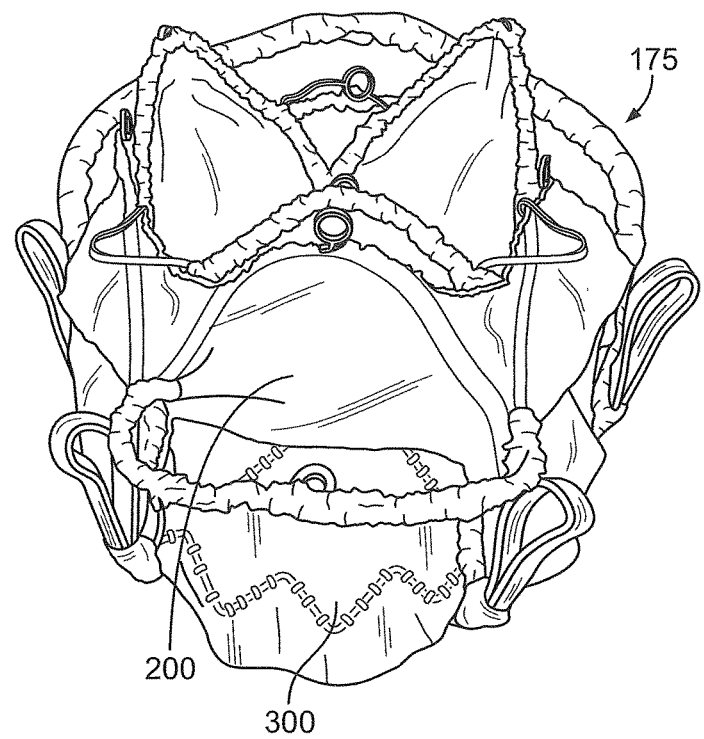
Figure 11D:
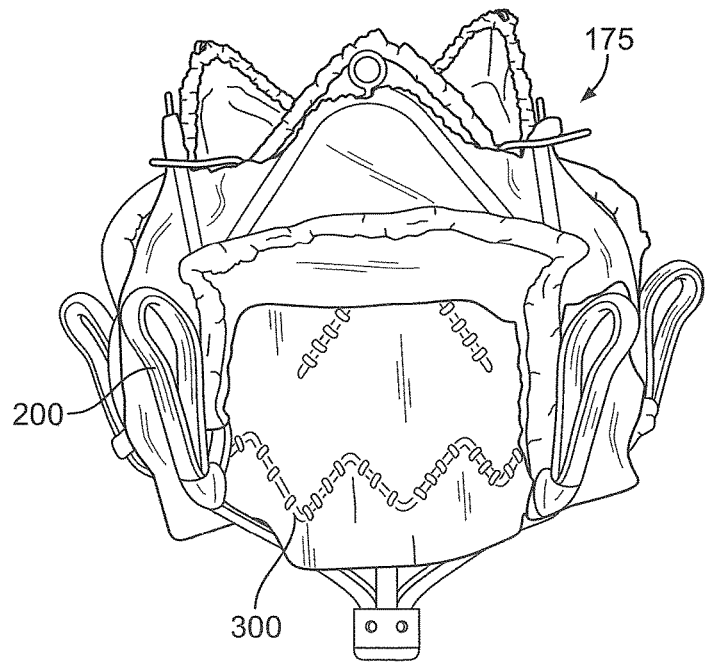

Further details concerning the gutter 120 can be understood from FIGS. 5 and 6, which depict a schematic cross-section of a left ventricle wall 140, a fibrous annulus 142 and posterior leaflet 144 of a heart. The gutter 120 exists both when the leaflet is open and closed and defines sufficient space to receive structure of an anchor device. FIGS. 7 and 8 provide further views of gutter space 120, indicating points where anchor structure 160 passes sub-valvular structure, and into the gutter. FIG. 9 additionally depicts a sub-valvular pocket 152 residing below the posterior leaflet (shown in a partially dissected heart), the same providing a convenient and effective space for receiving anchor structure. FIG. 10 depicts a V-shaped tent of chordae 154 connected to leaflets which again shows the space available for passing anchor structure into engagement with the gutter. Thus, a well-defined and distinct plane or virtual surface exists between the anterior chordae and leaflet and the posterior chordae and leaflets of the native valve which lends itself for the passage of a loop or similar frame structure without entanglement or loss of function.

Turning now to FIGS. 11A-D, there is shown various views of a complete anchor and heart valve assembly 175. The assembly 175 includes two basic components, an anchor assembly 200 and a heart valve assembly 300, each of which will be described more fully below.

It is to be noted that while various features of the anchor and valve assembly 175 have been shown and described below in connection with a number of different embodiments, any one or more features presented of one embodiment or approach can be incorporated into another embodiment or approach.

It is to be recognized that the mitral annulus is typically nonplanar, non-circular in shape, flexible and distensible. These all contribute to a complex substrate to effectively attach an artificial valve, and specifically the anchor structure. In this regard, there is contemplated a general cone-in-cone fit between the anchor and the artificial valve, the anchor receiving the artificial valve. The anchor will thus support the valve supra-annularly so that much of the structure of the artificial valve will not interact with native tissue. The first anchor is also equipped with arches that provide additional support to the frame to create a greater fatigue resistance. The anchor itself can thus include various approaches to support the skeletal structure. In one approach, the structure can be a supra-valvular structure with commissural feet. The commissural feet/projections can be structures which are multi-functional elements that can provide mechanical/geometric anchoring, penetration (needle/barb like) securement, and tissue based incorporation (in-growth) including subvalvular/sub-leaflet structures that extend into the LV wall, all of which do not interrupt leaflet, chordae or native valve function. Also, they can provide a positioning basis for the entire anchor because of their engagement with the commissural clefts in the anterior and posterior leaflets while still avoiding interaction or disruption of the chordae or native leaflets.

An anchor frame structure can be designed to provide a D-shaped or alternatively a relatively circular, non-distensible, non-elongating homogeneous frame substrate that the artificial valve can engage and attach to during its deployment. This structure may be continuous or interrupted, and completely around annulus or only partially around annular circumference. Moreover, portions of the anchor can be sinusoidal in plane of valve leaflets trying to create continuous attachment around entire circumference (each sinusoid comes in and out of plane) or sinusoidal perpendicular to valve bridging from point to point creating, multiple attachment points, thereby allowing for tissue ingrowth between sinusoidal points of native leaflet or annulus tissue contact/engagement. The anchor can be malleable with points of attachment between commissures, a single wire or multiple connected wire components, or be formed into a saddle configuration to approximate natural saddle geometry of valve (may be based off of 3d echo or CT to determine geometry).

There may further be a covering of the skeletal frame of the anchor. The covering of the anchor skeleton can provide opportunity for facilitating tissue ingrowth into or onto the implant structure and/or covering in locations such as on top (atrial side) of leaflet or annulus, at side of leaflets or annulus, at a ventricular wall at sub-valvular level, or underneath (ventricular side) of the leaflet or commissures.

A superstructure above the valve annulus may provide options for valve attachment to the anchor or even an alternative therapy such as mitral repair via a septal lateral cinch. Various superstructures above the annulus can include A2 P2 points of attachment, two circles to allow for double valves, or use of the atrial wall behind A2 or P2.

Materials for components used in multiple combinations and configurations, may include metals, especially for the anchor skeleton or frame structures such as Nitinol because of its superelasticity and ability to be compressed into a deliverable shape/state and then deployed into a functional state, titanium due to its strength and biocompatibility, stainless steel: hardened for its strength or malleable to aid in conforming to shape, cobalt/chromium alloy for strength and known valve component implant history; or composites to provide multiple properties based on anatomic location.

Tissue elements also may be incorporated on the anchor implant to aid overall function of holding or tissue engagement and sealing including pericardial (bovine, ovine, porcine) tissue or valve tissue (bovine, ovine, porcine). Further synthetic polymers can be used as biocompatible elements in implants and on the anchor due to their know tissue and blood compatibility properties. These can include Elast-Eon (a silicone and urethane copolymer), ePTFE, urethane, silicone, PEEK, polyester (PET), or UHMWPE.

Geometric/mechanical holding force for anchor that exploits the geometry/configuration of anatomic structures (relative to force vector) to achieve the necessary holding force required by a deployed artificial valve or other therapeutic element is further contemplated. The force vector encountered by the anchor structure's commissural projections provide a perpendicular load relative to the tissue. Commissural projections or foot elements that are able to deploy behind the anterior and posterior leaflets in the gutter where the leaflet meets the annulus provides for direct mechanical holding capability. The commissural projections of the anchor structure connected and bridged to each other provide an ability to hold the valve in position. LV wall projections of the commissural feet can provide for the ability to develop deep tissue penetration elements into the muscle, wider elements to increase surface area of contact/attachment, and longer projections to increase holding capacity. Moreover, because the projections can be placed such that they are supra annular and sub-annular, a C like structure in cross section can be utilized that is either connected or clamped. With regard to tissue penetration based securement, direct mechanical holding force is contemplated for an anchor that utilizes the natural strength of the LV and leaflet tissues to hold onto anchor structure. These elements can be configured to either be inserted into the tissue and resist pull out (barb like), or they may go into and out of tissue to provide a tissue "bite" like a stitch, or both elements can be employed. The structure can be located posterior annulus or entire annular perimeter, or adjacent leaflet tissue, the trigone/anterior annulus, an endocardial LV surface or LV Muscle tissue. Further, the tissue penetration securement elements can be linear (staple or nail like), helical (rotation axis is perpendicular to tissue interface or rotation axis is parallel to tissue interface (in/out/in/out)), curved and or curled, or bent (L shaped or S shaped).

As stated, it is also contemplated to use chronic ingrowth to provide long term stable implantation of the artificial valve and proper sealing function. In addition, chronic ingrowth of implant structural elements can serve as a fundamental mechanism to achieve the necessary holding force of the anchor functional element of the system. It exploits the natural healing response to foreign bodies placed into tissue and the blood stream to develop a strong collagen based tissue connection between the implant surface structures and the native valve tissue with a possible endothelial surface. This can be achieved while still managing the response to prevent unwanted damage to anatomic structures, damage to blood elements, or creation of thromboemboli.

More areas of consideration are the surface composition elements, specifically the material choice and texture to promote tissue reaction and device incorporation with maximal force holding capability. These elements can also be incorporated onto the tissue penetration elements to further increase the holding force by incorporation deep into tissue rather than just at the surface. The anchor can have a gross surface modification (barbs, slits), a surface texture/pores to promote ingrowth and mechanical hold, a fabric material covering (Dacron velour, double velour, ePTFE), a wire brush (multiple short wire elements) or an adhesive. There can further be a single or multiple points of attachment, planar attachment or by way of a confluent surface. Moreover, the tissue/anchor interface can be rigid or flexible and can include a wire frame structure that puts a compressive force onto surface contact interface to promote increased response. Also, tissue surface modification can include an abrasive, a chemical irritant to promote inflammatory response or application of heat.

In current conventional approaches to valvular intervention, a diagnostic echocardiograph is initially performed to assess valve function followed by two percutaneous procedures. First, a diagnostic angiography is performed with or without a right heart catheterization to assess, for example, whether they might also require revascularization first, prior to valve intervention. Here, patients do not receive valve therapy without the patient being fully revascularized. Thereafter, at a different time and place, valve replacement therapy is performed involving fixation/attachment, accomplishing a tissue sealing interface, and valve deployment and then release. In contrast, the presently described approach, however, can include an assessment involving a diagnostic echocardiography followed by a unique percutaneous valve procedure sequencing. First, a diagnostic angiography (±right heart cath) can be performed along with anchor fixation/attachment and anchor/tissue sealing. Subsequently, either later or during the same interventional procedure, valve replacement therapy can occur involving valve deployment and release. Thus, since the anchor implant allows the native valve to remain functional, the anchor implantation procedure could be added to the end of the angio (±PCI), and not require a separate interventional procedure. A quick, simple, and reliable anchor deployment could permit a fully ingrown structure that significantly enhances the holding force of a subsequently implanted replacement valve. Tissue ingrowth of the entire anchor perimeter, or at key positions thereon, can in fact provide the necessary tissue seal in advance of valve deployment. Moreover, the anchor design could be simplified due to less required acute holding force. Therefore, a tissue incorporated and healed anchor provides a structure to perform several methods of annular adjustment, including plication, reduction annuloplasty, and septal-lateral cinching.

Figure 12A:
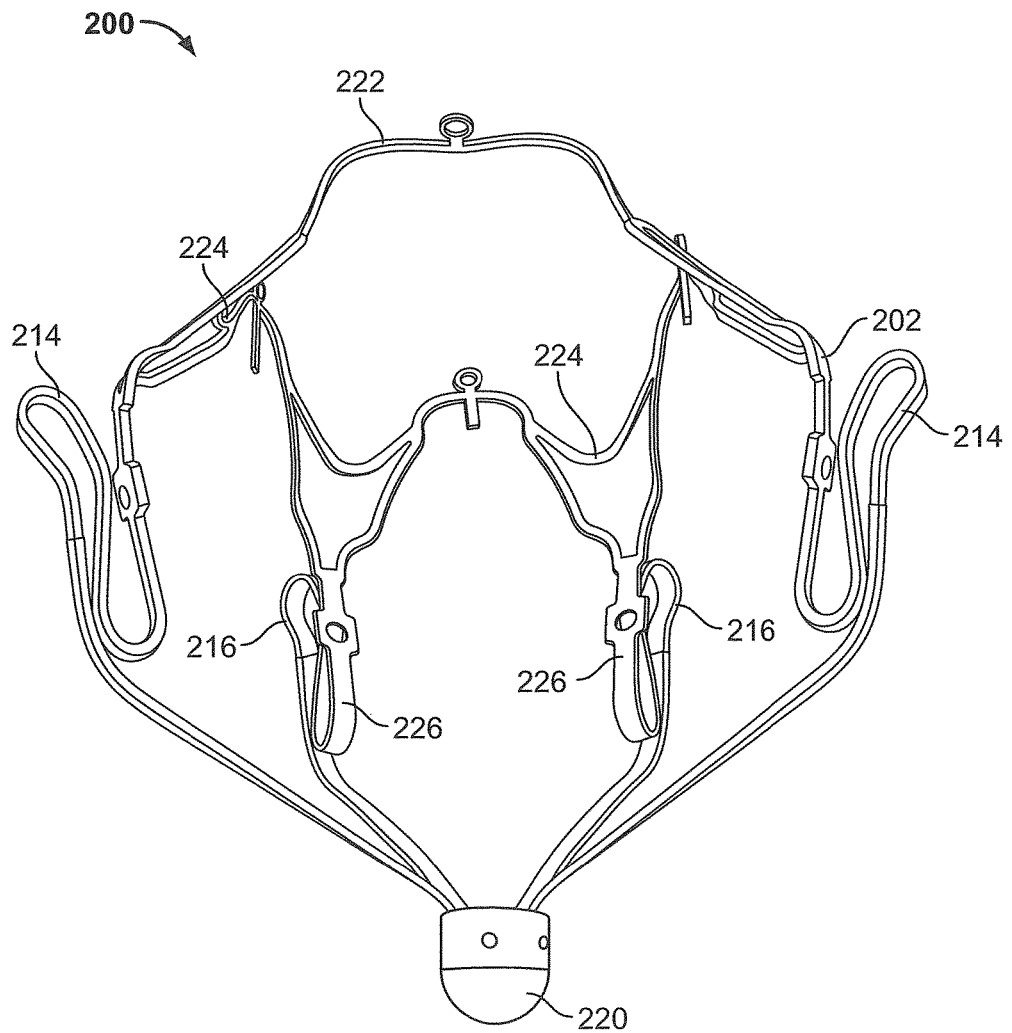
FIGS. 12A-C depict various views of one embodiment of an uncovered anchor assembly.
Figure 12B:
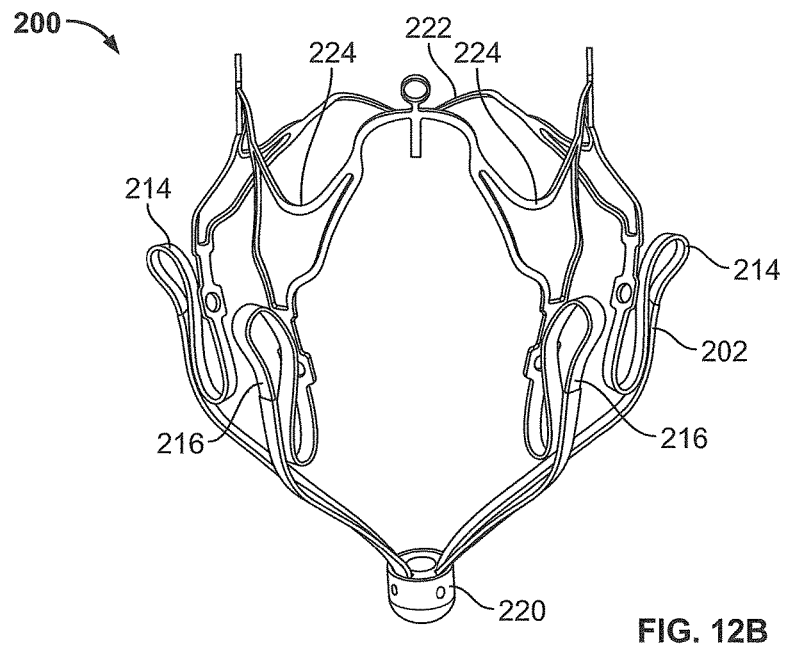
Figure 12C:
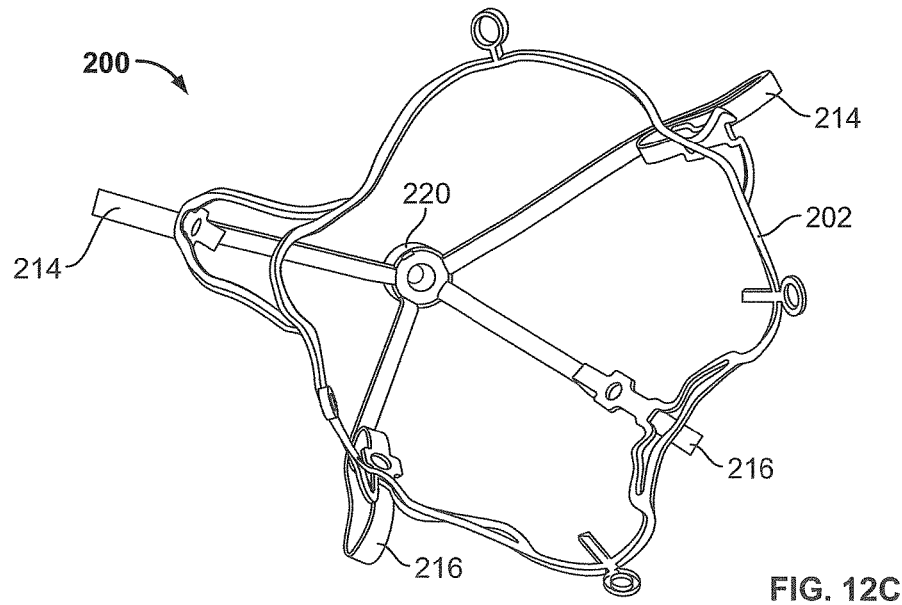

In one specific embodiment, the anchor assembly 200 can be embodied in a frame 202 including supra-annular and sub-annular structure (See FIGS. 12A-C). Here, the frame 202 is shown without a fabric covering. The anchor assembly is designed to not interfere with native valve function, allowing it to be placed some time prior to a replacement valve without degradation of valve function during the period of time between the anchor implantation and the valve implantation, whether that time is on the order of minutes, or even several days or months. It is also to be noted that the frame can be formed from a single continuous wire, or created compositely from multiple wires. The embodiment shown is fabricated from a laser cut tube, then shape set to its final expanded size and shape. The diameter or width of the wire or other structure (such as segments of a laser cut tube) forming the frame can range from up to 0.015 inches to 0.080 inches or more.

Extending from the frame 202 are a plurality of projections or feet 214, 216. Such projections are sized and shaped to engage the sub-annular, valve gutter described above. A first pair of projections 214 (anterior feet) are sized and shaped to each extend through one of anterior and posterior commissures and engage within or adjacent the trigone structure. In one approach, the projections can be spaced approximately 30-45 mm. Also, the projections can have a height ranging from up to 8 mm to 12 mm or more, and have a gutter engaging surface area (when fabric covered) ranging from 6-24 mm$^2$. The width of the projection can range from 1.5 to 4 mm or more and have a length ranging up to 4 mm to 6 mm or more. A second pair of projections 216 (posterior feet) are also provided. A distance between the first and second pair of projections can be about 20-30 mm. The projections 216 are sized and shaped so that when implanted they avoid interference with mitral chordae, valve leaflets, and papillary muscles. Terminal ends of the projections are further configured to be sized and shaped to be received within and engage a posterior portion of the sub-annular gutter (as shown and described above).

The sub-annular structure of the anchor frame 202 further includes a central hub 220 which can both function as structure employed as a releasable connection during device delivery, as well as a base from which sub-annular support arms 252 extend, one to each projection 214, 216. With specific reference to FIG. 12A is an anterior view of the anchor 200, one can appreciate the more widely spaced anterior feet 214. The anterior feet create the widest sub-annular dimension of the anchor. In FIG. 12B, the anchor 200 is shown in a posterior view, one can appreciate the arches 222 beginning approximately at the level of the tip of the projections 214 and extending atrially upward. FIG. 12C shows the device from the top and slightly from the lateral side. In this view one can appreciate the sub annular support arms 252 extending radially for the central hub to the projections 214. Connection bridges 224 between arches 222 provides enhanced stability and fatigue resistance from vertically oriented forces on a companion artificial valve when the valve (not shown) is closed and blocking pressurized blood during systole. The assembly 200 can also include holes 226 in frame portions adjacent the feet, which are additional control points for delivery and retrieval of the assembly, or could be used to secure a positional delivery frame.

Figure 13A:
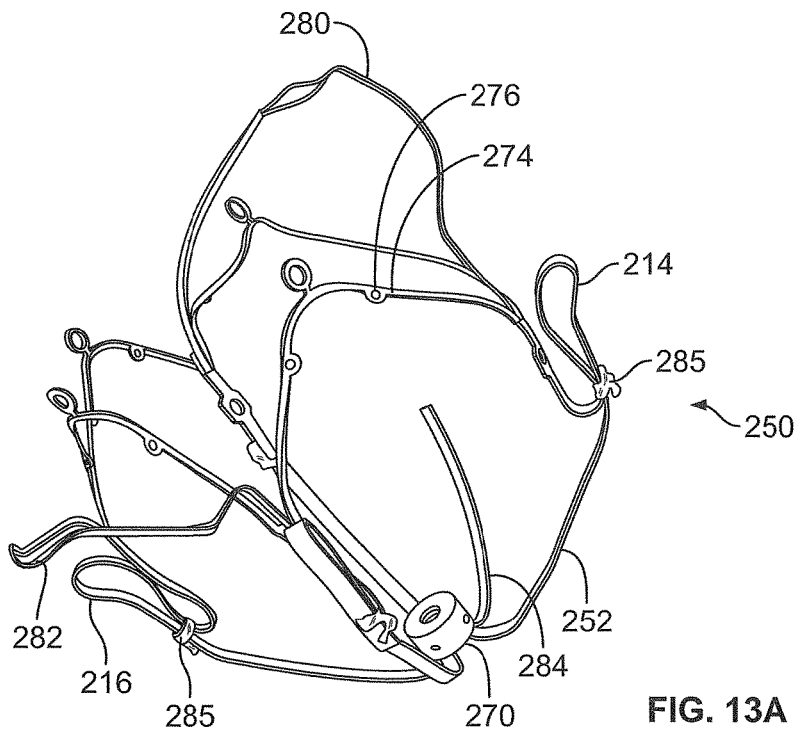
FIGS. 13A-D depict various views of another embodiment of an uncovered anchor assembly.
Figure 13B:
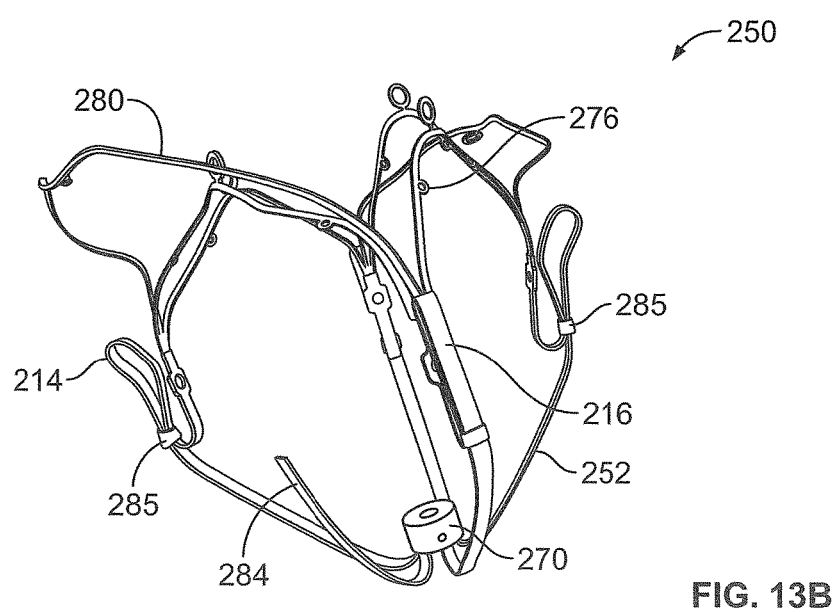
Figure 13C:
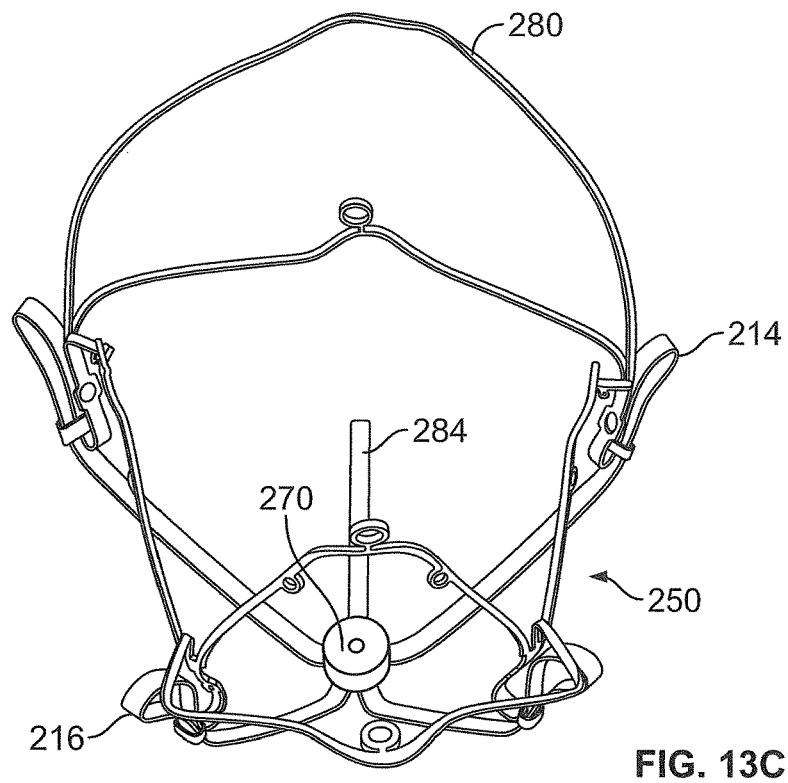
Figure 13D:
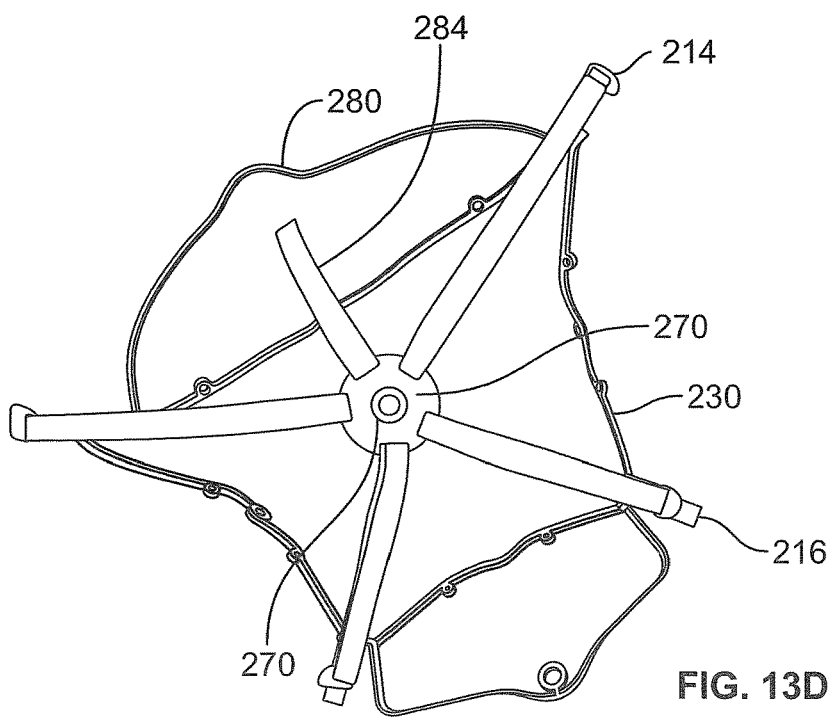
Figure 14A:
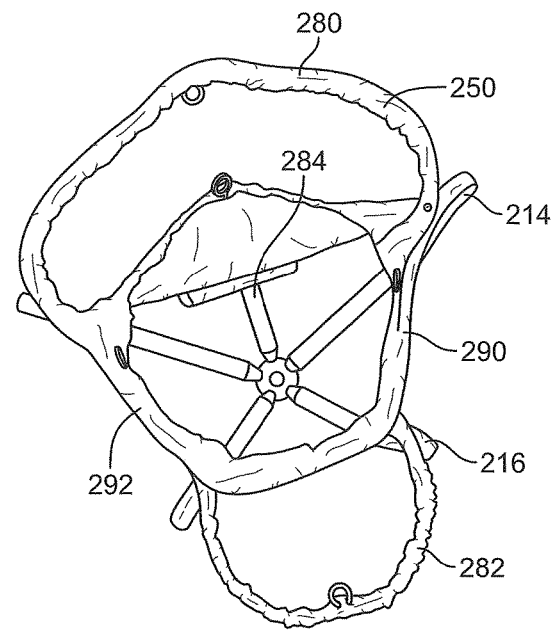
FIGS. 14A-D depict various views of the anchor assembly of FIGS. 13A-D covered with fabric.
Figure 14B:
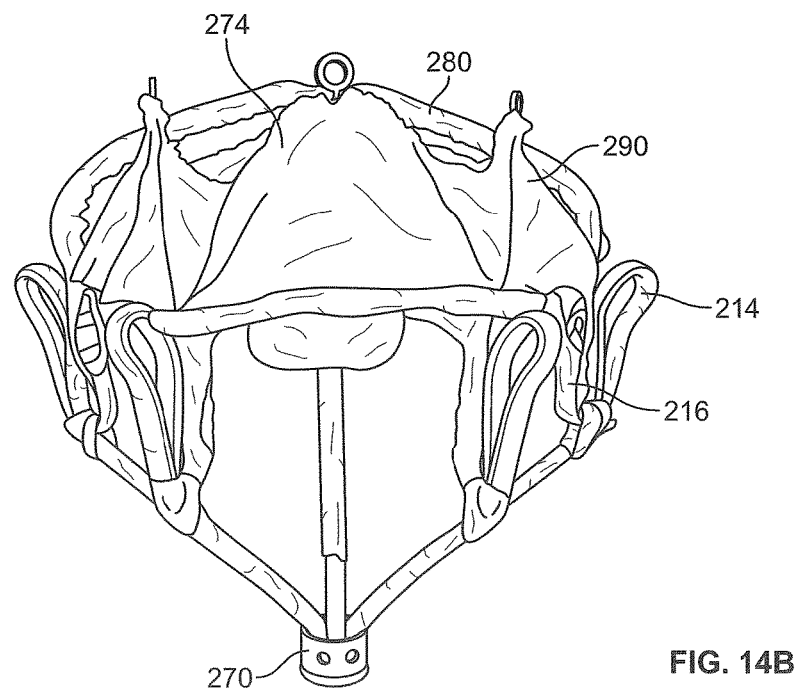
Figure 14C:
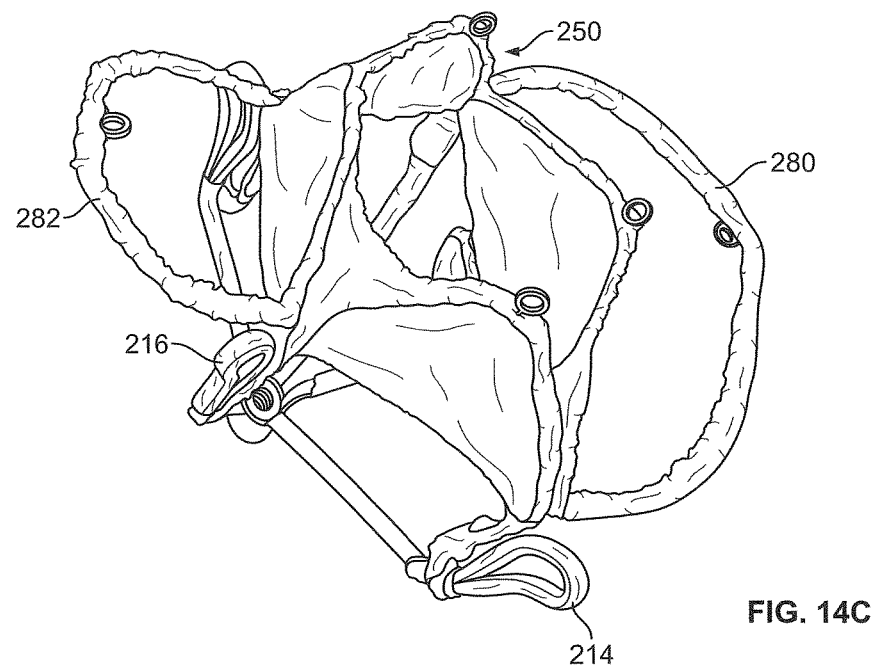
Figure 14D:
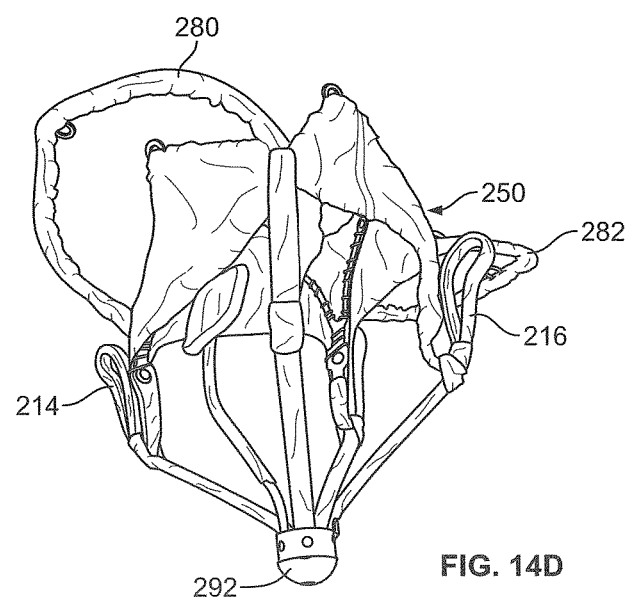

In an alternative embodiment of an anchor assembly 250 as shown in FIGS. 13A-C, a wire frame 252 includes atrial stabilization and systolic anterior motion (SAM) stabilization features. The diameter or width of the wire or other structure (or laser cut tube segment) forming these structures can range from up to 0.015 inches to 0.060 inches or more, or up to 0.025 inches to 0.080 inches or more, respectively. Turning specifically to FIG. 13A, the anchor 250 is shown in a posterior medial view, it can be seen that the assembly 250 further includes both an anterior atrial stabilization feature 280 and a posterior stabilization structure 282 design. In the anterior lateral view, FIG. 13B, one notes that arches 274 do not have bridge supports, but rather holes 276 for suture securement to prevent excessive outward motion of arches during systole. In FIG. 13C, top view and slightly posterior view, one call visualize the SAM feature 284, extending anteriorly and superiorly is further provided to prevent a natural anterior leaflet from "flopping" outward into the aortic outflow tract. Here also, the distal hub 270 is inverted. Further, the bases of the feet loops 214, 216 are sutured 285 together to add stability to the feet and minimize fatigue forces. As best seen in FIG. 14A, the atrial stabilization frames 280, 282 can be included and an entirety or less than an entirety of the frame can accept a fabric material there across. Fabric or other sheet material can also be included to fill the open arc created by the atrial stabilization frames 280, 282. Notably, the atrial stabilization structure 280, 282 provides stability from downward forces during left ventricle filling. In the posterior view, FIG. 14B, it can be seen that fabric or other sheet material can cover all or part of the area created by the arches 274 to facilitate durable contact with the prosthetic valve. FIG. 13C shows the anchor 250 in posterior medial view slightly from above, one can further appreciate the anterior 280 and posterior 282 atrial stabilization frames and their relationship to the feet 214, 216. The anti-SAM feature 284 and its attachment to the hub 292 can be best depicted in the anterior lateral view and slightly from the bottom, FIG. 14D.

With reference to FIGS. 14A-D, there is shown an embodiment of an anchor assembly 250 with covering 290 to facilitate tissue ingrowth. It is to be noted that this embodiment has a fabric ring-like structure, connected between anchor arch supports for facilitating securement of the later deployed valve structure. This anchor embodiment also includes the two atrial stabilization features 280, 282 as well as the anti-SAM feature 284, which is covered, and also has an elongated bumper. Arches in this embodiment can be stabilized by optional sutures interconnecting between the arch segments. The hub 292 is not inverted in this assembly, but may optionally be inverted.

As stated, staging is the ability to stage the implantation of valve structure so that it could be deployed in the same procedure as that of the implantation of anchor and sealing structures, or thereafter. As the anchor and sealing structures grow into and are incorporated in the tissue/existing anatomy, the holding capability of these structures increases until such time as the valve/assembly is deployed, either automatically (e.g., suture dissolving over time) or by some trigger mechanism or actuation during a second procedure. This actuation could be achieved remotely without invading the body (e.g., RF or ultrasound-like actuation).

The valve replacement system according to the present disclosure allows for valve delivery flexibility. Specifically, tissue valves can be delivered either via a fully percutaneous procedure or a minimally invasive surgical delivery of the valve without modification to the valve implant to accommodate the alternative route.

Yet another aspect of having a stable consistent anchor platform for receiving a valve structure is that it allows for valve sizing that is appropriate for the patient population (FMR, structural, mixed) and even specific to the patient being treated. In other words, it allows for the largest valve possible in every patient rather than compromising size (smaller than physiologically desired) to accommodate technology limitations in systems that must combine multiple (increase complexity) valve, attachment, sealing and delivery structures.

The system according to the present teachings also allows for therapeutic flexibility of the artificial valve. The presently disclosed system allows for beating heart implantation of both tissue and mechanical valves. It is thus, contemplated that delivery systems are provided that allow implantation of mechanical valves via either a trans-apical or trans-atrial thorascopic route.

Moreover, while surgical tissue replacement valves in the mitral position have conventionally often been basic and inverted modifications of the tri-leaflet aortic counterpart, the percutaneous delivery requirements (collapse/expand) of the TMVR allows for designs specific to mitral position on several functional requirements. For example, there is sufficient size for blood inflow so as to not trade regurgitation for stenosis. One key aspect is that in functional MR with native annular dilatation, the replacement valve does not need to fill the whole annular area of the now dilated annulus. A smaller area can be used while still creating sufficient size to prevent any inflow obstruction/stenosis. Also, it is desirable to maintain LV chordal connections and geometry to maintain LV functional geometry and stress configuration. Cutting or disruption of the chords can create significant increases in LV wall stress and resultant loss of cardiac function.

A durable valve design balances sufficient valve height relative to the diameter to prevent excessive post loads and leaflet stresses. In the mitral position (vs. aortic) this is accentuated with the generally larger valve diameter requirement (lower through flow pressure) and the higher valve loads encountered when closed (LV systolic pressure vs. diastolic aortic pressure). In surgical replacement mitral tissue valves, the valves are designed for the base to be sewn to the annulus with stent leaflet posts extending downward (into LV) from the base. Leaflet posts are designed to be short to minimize LV depth and prevent outflow tract obstruction or native leaflet entanglement. In these valves, the base also tends to be designed as a cylinder and therefore is not extended into the atrium to prevent potential pockets of stagnated blood.

Sealing against the native valve is to be a consideration. A valve that relies on radial expansion and or compression to create the seal requires a valve frame that is larger than the native annulus and exerts radial force to create the interface. Sufficient anchoring interface and holding is also an important consideration. Valves that rely on frictional interface to create anchoring force require relatively larger radial expansion force capability increasing the complexity of the stent frame. Ability to collapse into a deliverable configuration and then reliably expanded configuration can be addressed as well as the prevention of LV outflow tract obstruction. Too great of an encroachment into the LV beyond the native mitral annulus can impact the position and function of the native anterior leaflet. If it is pushed too far down and out, it can directly reduce the dimension of the LV outflow tract and/or allow the non-functional native anterior leaflet to be pulled into the outflow tract during systole creating functional obstruction of the LV outflow tract. Moreover, prevention of flow stagnation regions to prevent clot formation and embolization can be important on both the atrial side as well as the ventricular side, specifically in the sub-leaflet gutter region.

Regarding these final two considerations, aortic valves that are being modified to use in mitral position as well as surgical valves conventionally all have a generally tubular design at their base region or beyond up into the commissural post region. This tubular design that bridges across the native mitral valve has the possibility of creating outflow tract obstruction and pockets of stagnation behind the valve and native leaflet region if it extends too deep into LV or can create significant flow stagnation regions if the "tube" extends too far into atrium with blood having to flow up and over the valve base to reach LV during diastole. Additionally, the use of a tubular symmetric valve in a D-shaped mitral annulus may distort the prosthetic valve shape result in uneven distribution of stresses across leaflets and therefore reduced durability.

Thus, in one contemplated embodiment of a percutaneous replacement mitral valve, there is structure for facilitating an optimum valve for the mitral position. With respect to atrial biased positioning, the contemplated valve is positioned with a bias to the atrial side with the LV side only extending to or short of the commissural and posterior leaflet tips when they are in the diastolic position (vertical to LV wall). This allows for minimal interference with native leaflets and chordal connections, minimizing engagement and interference with the anterior leaflet therefore minimizing potential for outflow tract obstruction, minimizing sub-leaflet (LV side flow stagnation and potential for clot formation and embolization, and allows for sufficient valve height to manage commissural post strain and leaflet stresses. Taller or longer leaflets for a given valve diameter have smaller leaflet stresses.

The contemplated approach is also contemplated to embody a "ring in ring" stent design. Here, this is an inner ring for large circular leaflet/occluder geometry for optimum function and durability. The inner ring can consist of the 3 commissural posts joined by the 3 arches and the 3 leaflet cusps sewn to the posts and arches. This structural relationship that allows the outer ring to deflect and adapt to the non-circular native anatomy while maintaining circular inner geometry allows for overall better valve performance and maximizes durability. Another aspect of this configuration is that the leaflet excursion during diastole where the leaflets define a circular shape is that the leaflets do not impact or come into contact with the outer support frame/ring reducing the likelihood of damage to the leaflet tips as can happen with an overall circular support frame. Moreover, it is contemplated that the leaflets can be formed from glutaraldehyde fixed pericardium or aortic cusps from one or more of a bovine, porcine, ovine or equine, and having a thickness of 0.005-0.020 inches or specifically between 0.008-0.012 inches and being anisotropic (collagen fibers circumferentially oriented) such that modulus in one direction is higher than another (E circumferential>E radial).

The replacement mitral valve also includes central support of commissural posts (vs. base) to minimize cyclical strain and improved durability. Loading during leaflet closure is translated to the posts and creates tip deflection toward the valve center. Having the posts supported more to the middle of the overall stent frame helps minimize cyclical strain and therefore improves durability. The longer posts and leaflet height combine with a more centrally supported post to improve overall durability due to more uniform distribution of stresses between the leaflets. Further provided is an outer ring for adaptable sealing interface and native valve engagement. The outer ring can adapt to the native leaflet and valve shape and size while maintaining the central core inner ring.

The contemplated replacement valve can also include a scalloped or arched leaflet cusp design. With the more atrial positioned valve, the scalloped arches or cusps help minimize atrial flow stagnation both during diastole when the leaflets are in the open position, the blood flows between arches which sit proximate the native annular height, and during systole as the backside (non-leaflet side) of each arch is also pressurized and creates dynamic motion behind the cusps. Traditional tubular design valves have no such capability. With the leaflet cusps sewn to the arches, there is also efficient load transfer from the leaflets to the arches and then to anchor structure, also minimizing stent deflection/strain and enhanced durability.

The replacement valve is also contemplated to include structure for engagement with the anchor. In this way, an interlock of supra-annular structure is presented. In one approach, a cone-in-cone fit is employed to create the interlock. This structure of the valve engages with the anchor structure to provide for a described geometric interlock for load transfer to the anchor rather than frictional fit to anchor or the native valve. Therefore, the radial strength of the valve is less than required if a frictional fit was used; it needs to be properly sized, but does not require radial force expansion into the anchor ring.

Additionally, collapsibility, expression, repositioning, and recapturing of valve are all further requirements or desirable aspects of the overall valve design. The current embodiment has several elements that contribute to an improved capability to perform these functions. That is, the potentially lower radial force required for the overall valve design can allow the valve to collapse with less force both initially during insertion into delivery catheter, as well as when the valve may need to be partially collapsed for repositioning, or fully collapsed for recapture and removal. Also, the arches of the valve create an improved leading edge (rather than a collapsed cylinder) for the valve to be retrieved into the delivery sheath if needed, provide natural points of holding and individual control during expression and deployment, and provide lower regional outward radial force that facilitates holding during deployment into the anchor as well as during recapture. The arches or scallops can allow the valve to partially function during placement for a more controlled implant with less potential for negative hemodynamic consequences to the patient. Also, attachment to the arches allows for functional assessment of valve prior to final release. The three points of proximal hold also create the ability to control the planarity of the valve so it becomes coplanar with the anchor prior to full deployment. The three inner posts also may provide a distal holding point during delivery.

Accordingly, referring to FIGS. 15A-F, there is presented one particular approach to a valve 300 embodying a number of the above-identified desirable valve features. Various views of the valve frame 310 alone are set forth in FIGS. 15B and C provide a sense of its overall structure. The frame 310 of the valve 300 defines a generally D-shaped inferior opening and the flat edge is intended to correspond with an anterior portion of a natural valve annulus, and includes an undulating ring 312 having three leaflet arches 314. Each arch 314 defines a generally parabolic profile having a loop 316 at its apex and adjacent arches 314 being connected at their bases to form commissural posts 318. In one particular embodiment, the members defining the frame have a thickness of up to 0.012" to 0.024" inches, and can be in the range of 0.016"-0.018" inches.

Figure 15A:
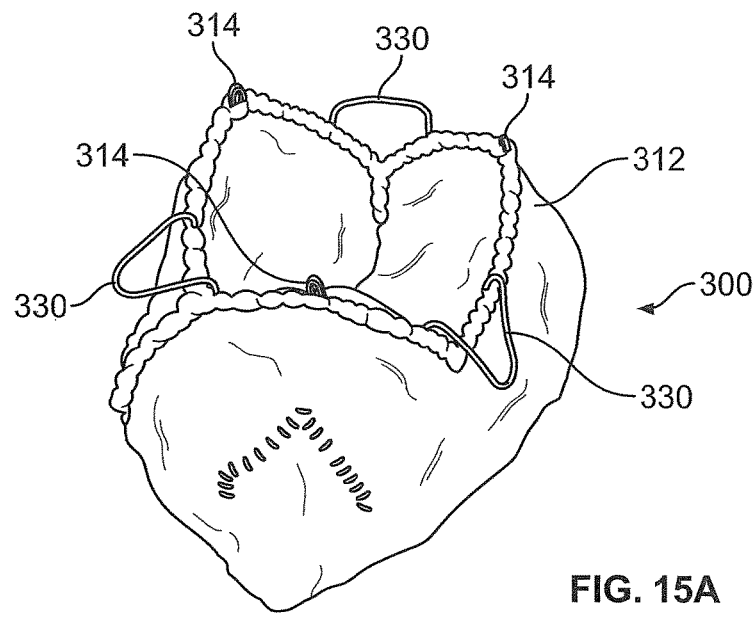
FIGS. 15A-F depict various views of a valve assembly with and without tissue covering and leaflets.
Figure 15B:
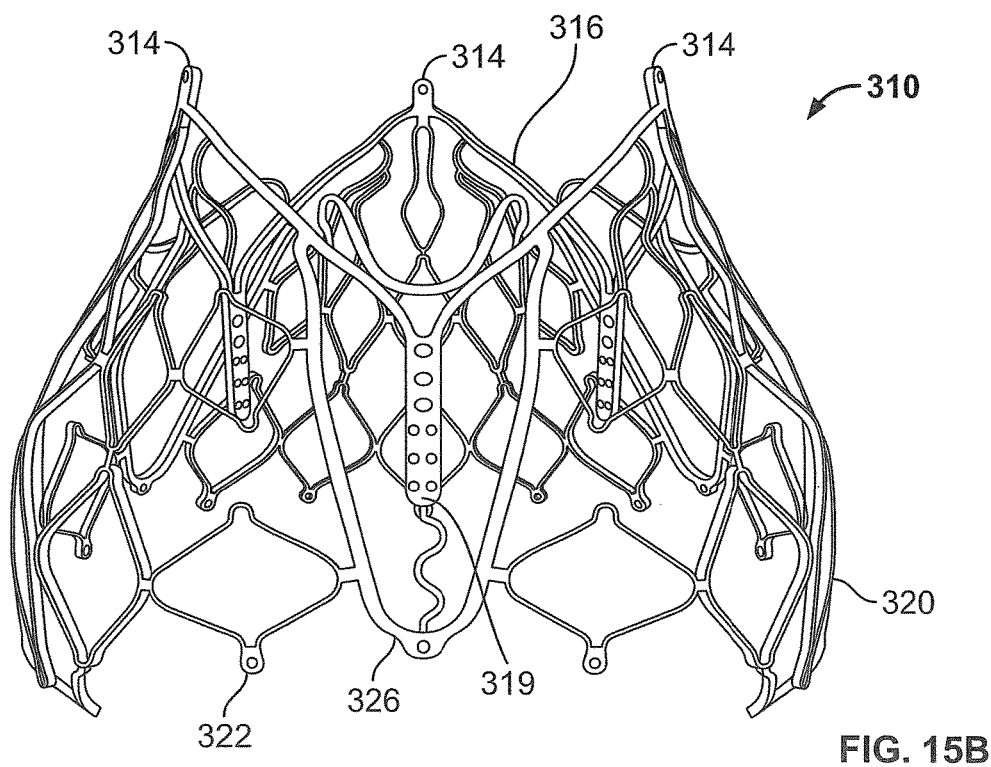
Figure 15C:
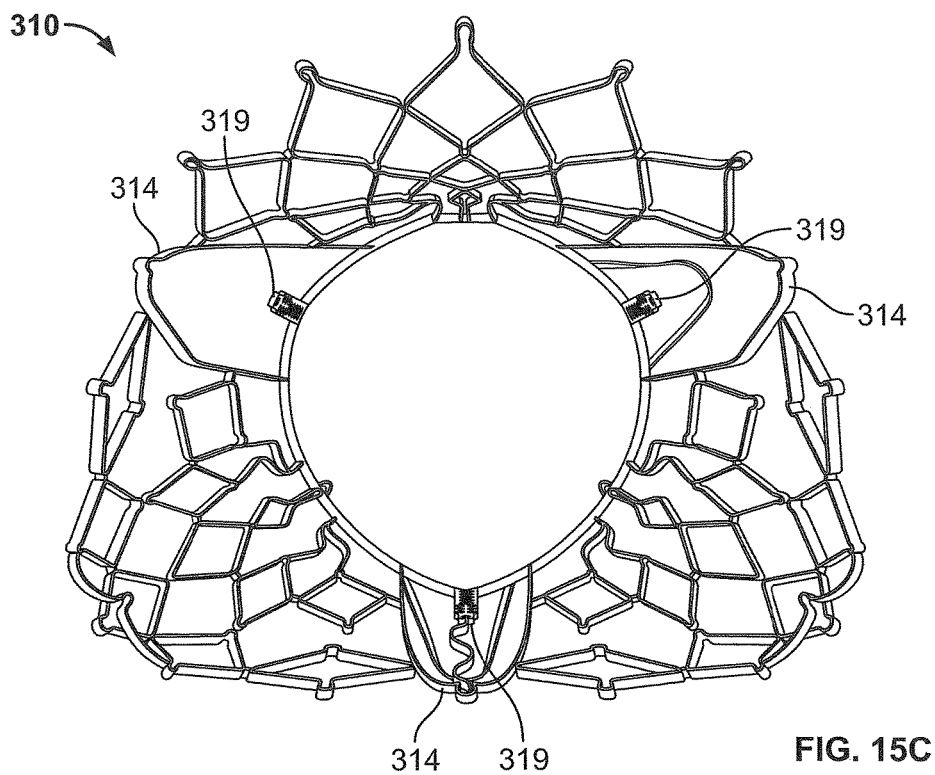
Figure 15D:
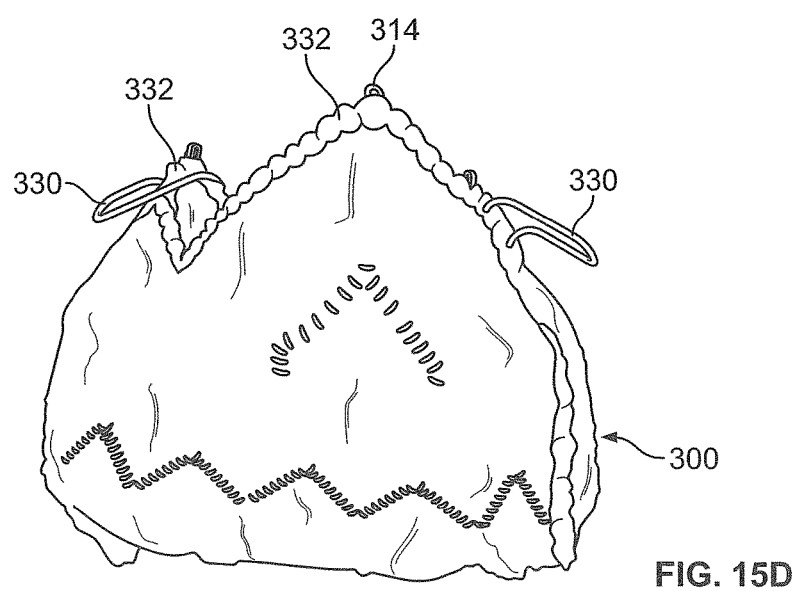
Figure 15E:
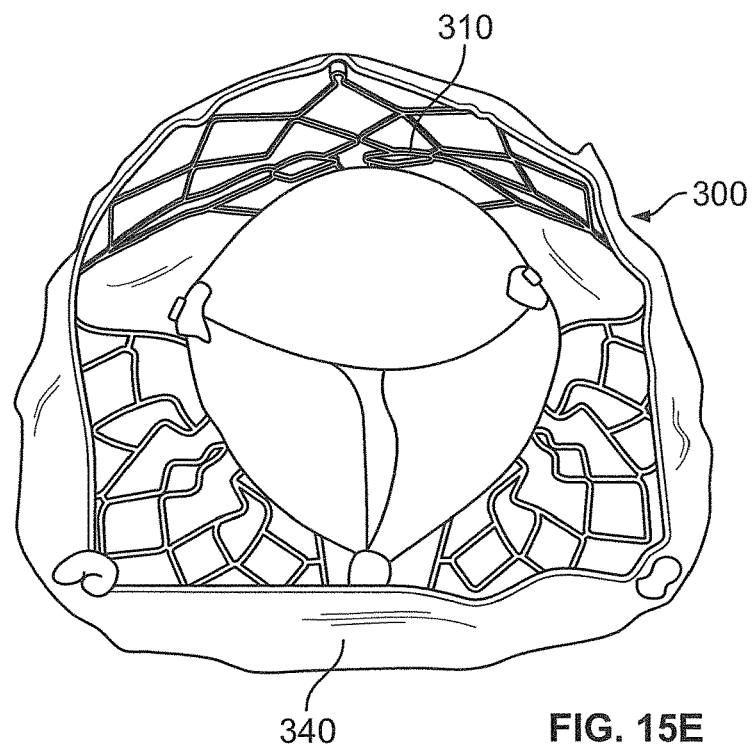
Figure 15F:
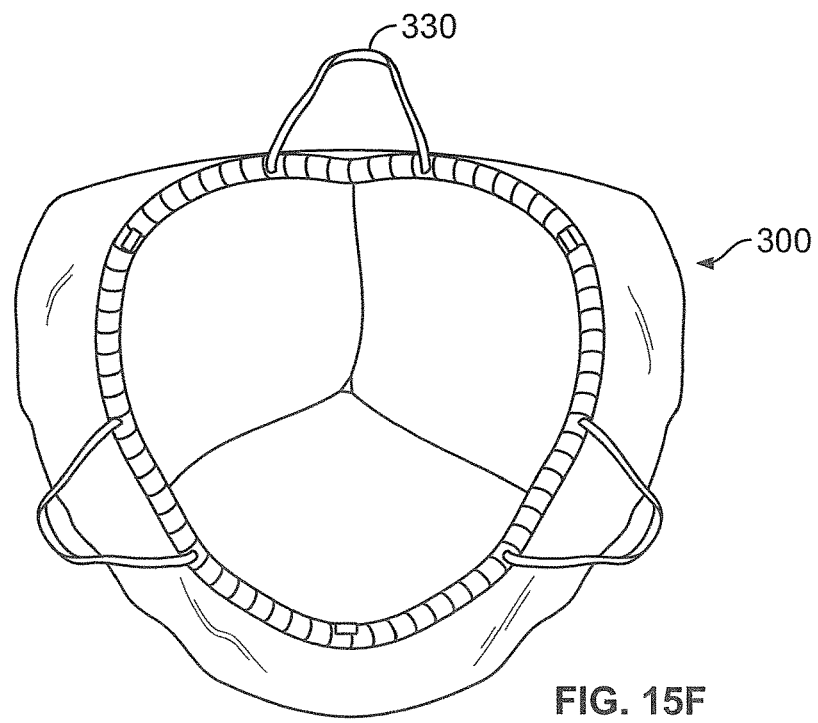

With specific reference to FIGS. 15B and 15C, various features of the valve frame 310 can be best appreciated. As shown in FIG. 15B, an external aspect of the frame 310 assumes a general conical aspect when viewed from the side. Extending inferiorly from lower portions defining the connection between each adjacent arches 314 are posts 319 which together define a circular orifice (FIG. 15C). When the tissue making up the leaflets are secured thereto, and in an open valve state (not shown), the open valve defines a cylinder. Moreover, as shown in FIG. 15C, viewing from an inferior side, one can appreciate that the portion of the frame 310 corresponding to the anterior part of the native valve annulus is flatter. Thus, from this view the D-shape of the inferior aspect of the frame can be seen, together with a circular orifice for attachment of the prosthetic valve leaflets. From an inferior aspect, as shown in FIG. 15E, an inferior edge 340 of the valve assembly 300 serves as a sealing surface against which the native valve leaflets contact during systole. Longer term, the native valve leaflets fuse to this edge for robust sealing. Also, again it is noted that the inferior edge is generally D-shaped, but the valve orifice is circular.

The frame 310 includes a plurality of rows of closed cells 320. Although the cells 320 can assume various shapes, as shown, when expanded, each cell includes upper and lower narrowed ends and a wide mid-section. Additional support is provided by members 322 extending from the arches 314, to thereby define a larger V-shaped cell 326 encompassing each of the posts 319. Further provided are loops 330. Such loops can be included for strength or integrity and can be connected to adjacent arches 314. Loops 300 may be configured to hook over adjacent portions of the anchor for positioning control, as can be seen in FIGS. 11A-D. As best seen in FIG. 15D, delivery control points in the frame of implants 332 can be positioned at the apices of the arches 314. Furthermore, taking a view from a superior aspect (FIG. 15F) of a valve assembly where the leaflets are shown in a closed condition, one can note the difference in size and shape between the valve orifice compared with the external frame and skirt.

Figure 16A:
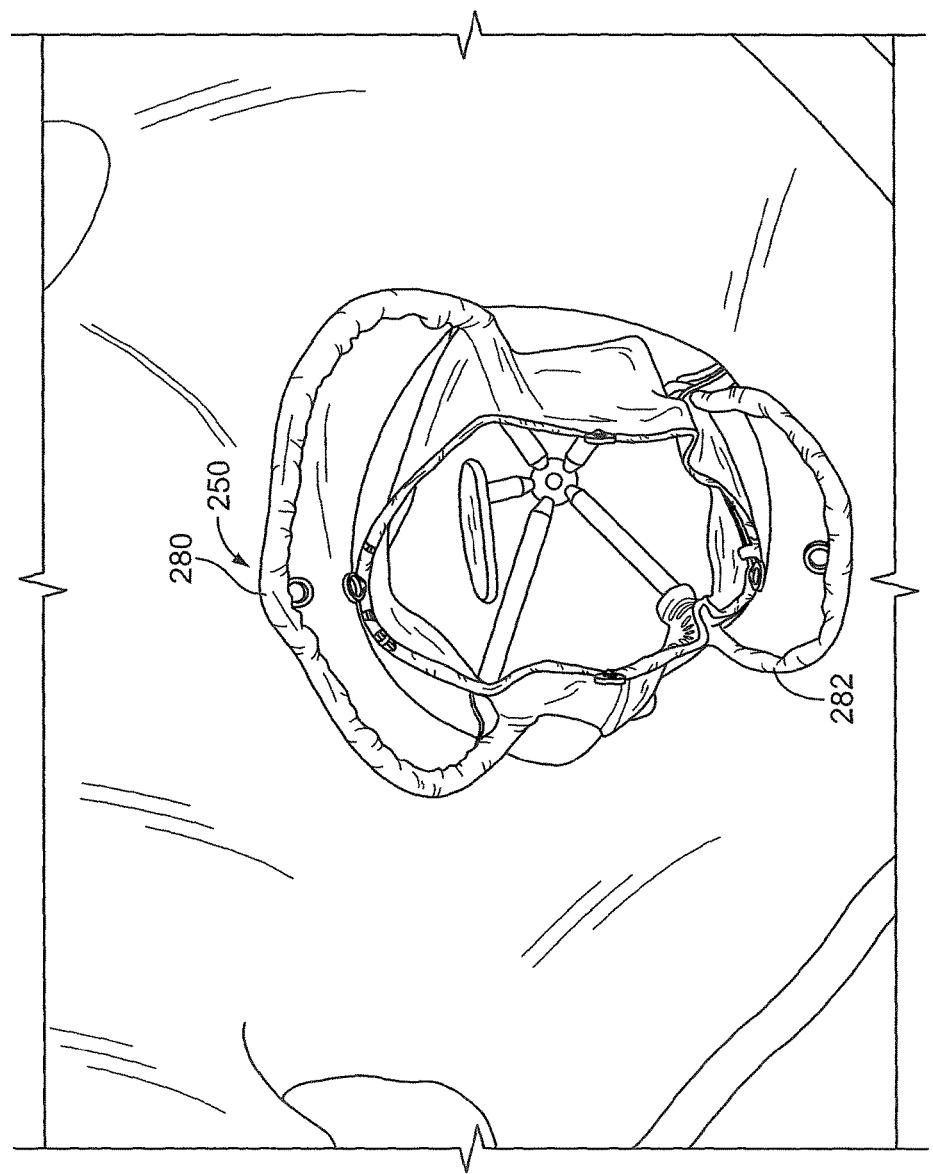
FIG. 16A depicts a covered anchor assembly in simulated anatomy shown from an atrial viewpoint.
Figure 16B:
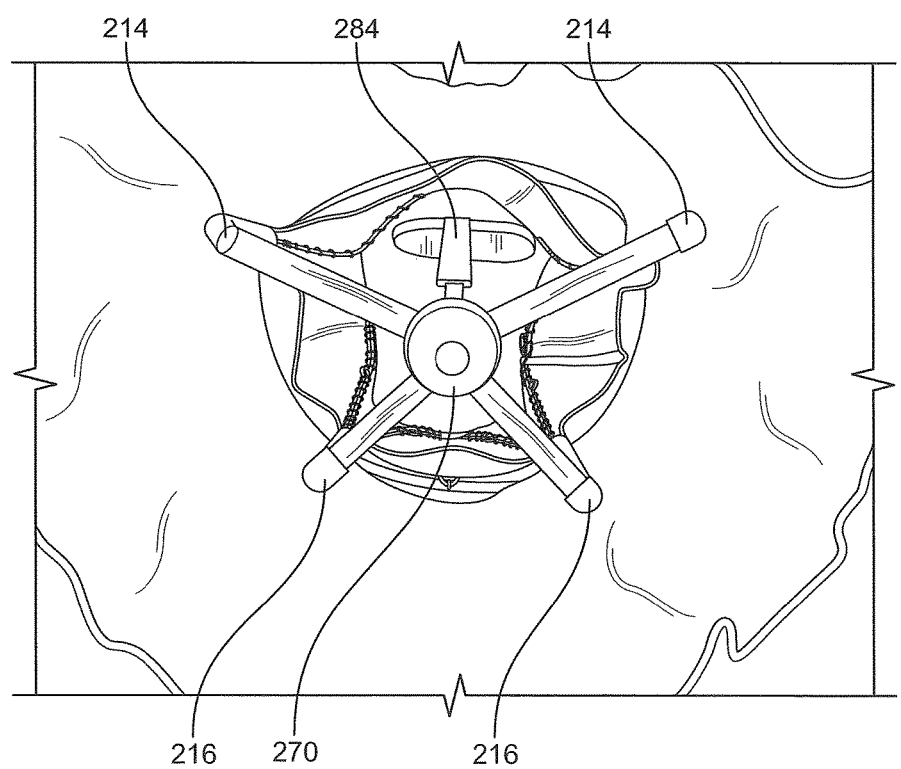
FIG. 16B depicts the covered anchor assembly of FIG. 16A in simulated anatomy from a ventricular viewpoint.

Turning to FIGS. 16A-19, there are shown various views of the disclosed anchor assembly placed in anatomy or structure simulating anatomy for illustration purposes. Referring in particular to FIG. 16A (view from atrium) and B (view from ventricle), one embodiment of an anchor assembly 250 with covering is shown in anatomic depiction of mitral valve annulus. Two of the feet (anterior) 214 are hooked under the gutter near the trigones, and two of the feet 216 are hooked under the gutter behind what would be the posterior leaflet (native valve leaflets not included in this simulated anatomy). The anterior leaflet of the native valve would be engaged by the anti-SAM feature (FIGS. 16A-16B). It is further noted that the atrial stabilization features 280, 282 are in contact or close to contact with the atrium above the annulus, to facilitate tissue ingrowth (FIG. 16A).

Figure 17A:
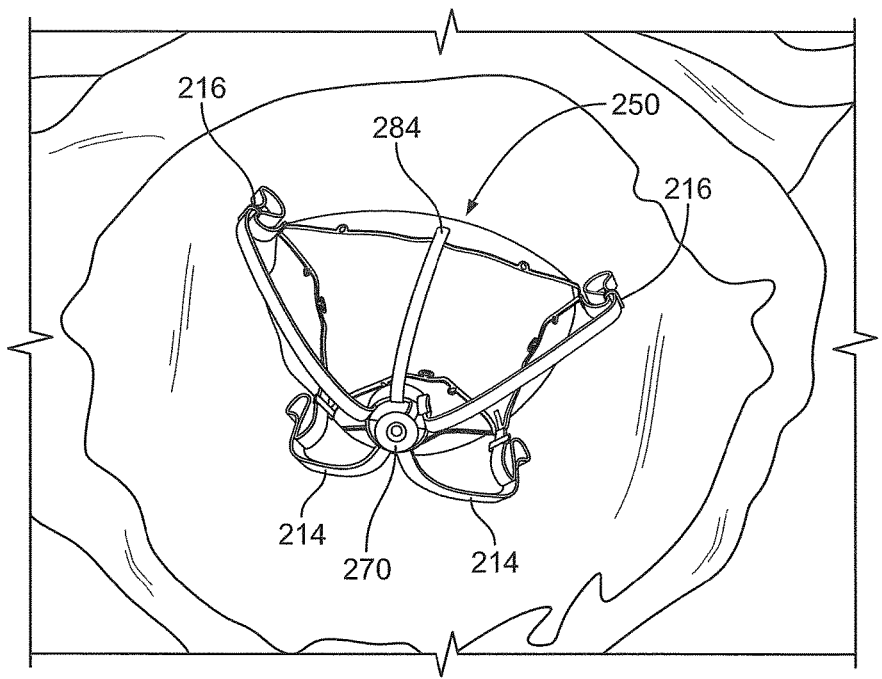
FIG. 17A depicts an anchor assembly without a fabric covering, in simulated anatomy from a ventricular viewpoint.
Figure 17B:
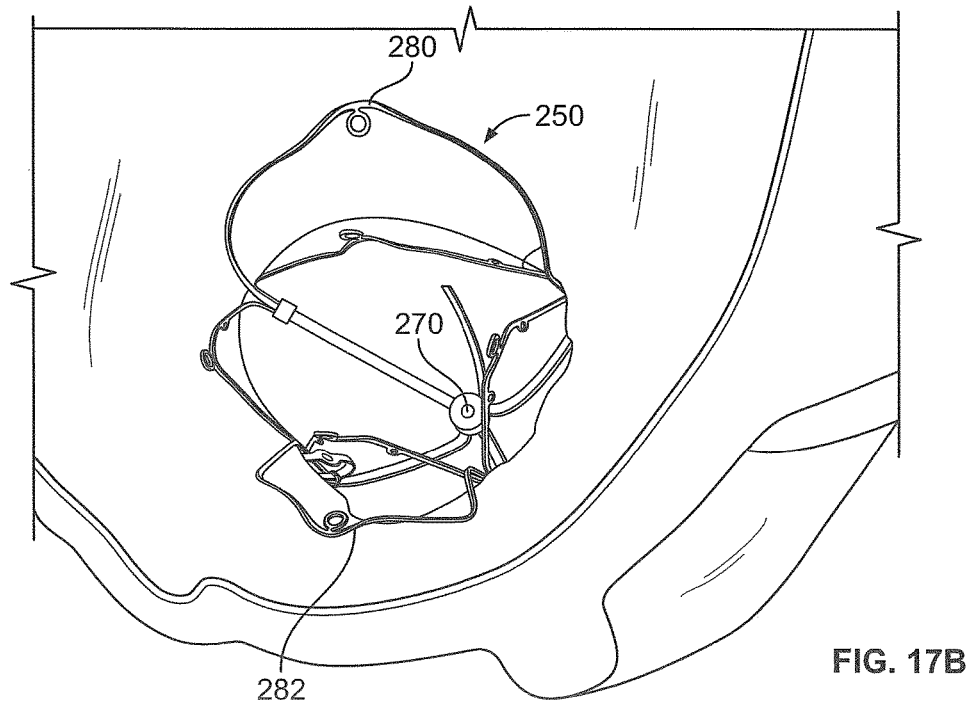
FIG. 17B depicts the anchor assembly of FIG. 17A from an atrial viewpoint, in simulated anatomy.
Figure 18:
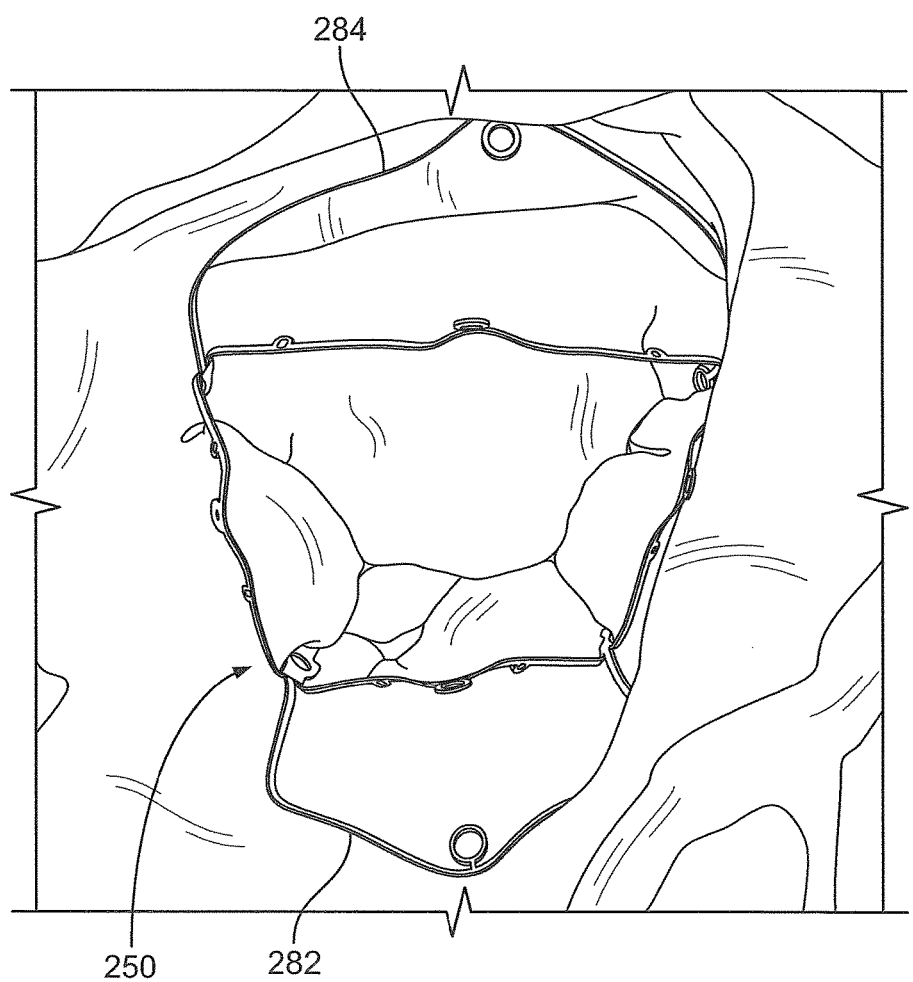
FIG. 18 depicts another view of an uncovered anchor assembly in anatomy from an atrial viewpoint.
Figure 19:
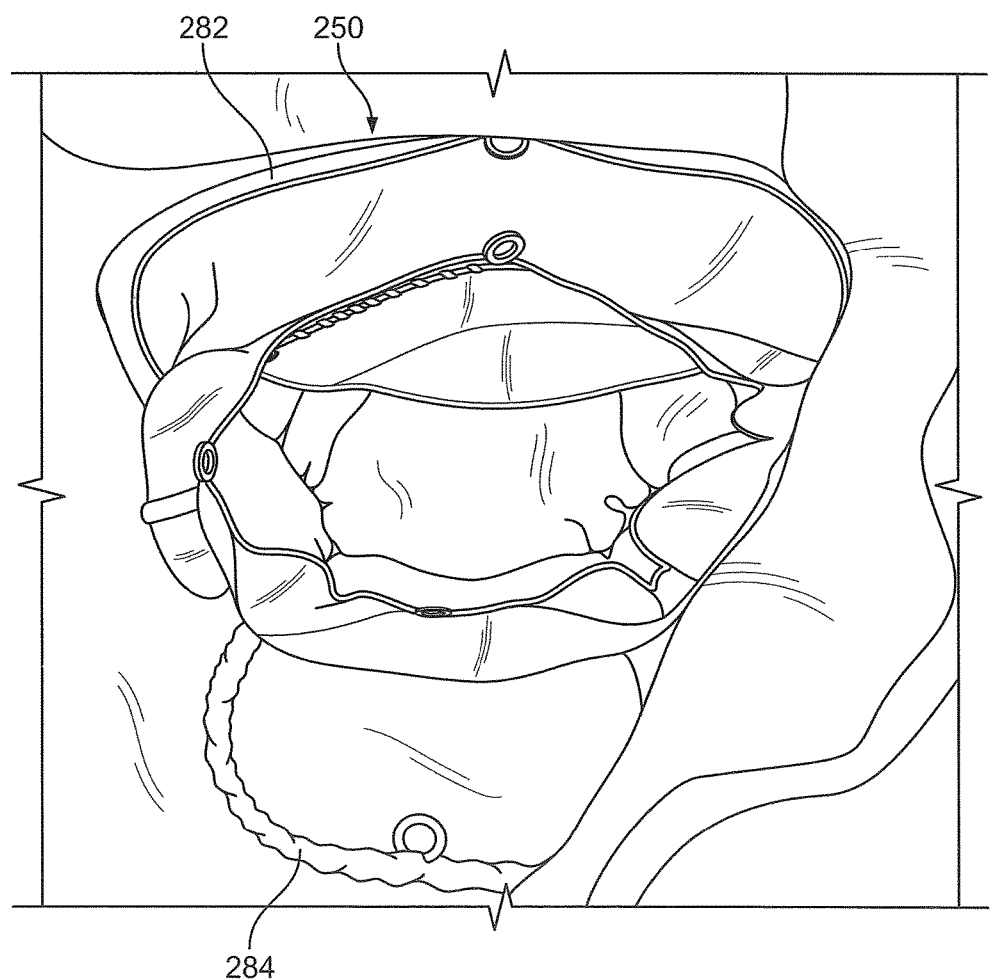
FIG. 19 depicts another view of a fabric covered anchor assembly within anatomy from an atrial viewpoint.

For illustration purposes, an uncovered anchor (embodiment) is shown in simulated anatomical structures (See FIG. 17A (view from ventricle) and 17B (view from atrium)). It is to be noted that the native valve leaflets can seal up against anchor structure 250 that extend sub-annularly, as can be seen in FIG. 18 (view from atrium of a porcine heart). The two anterior legs and feet 214 are within or near the commissures, allowing for relatively normal functioning of the anterior leaflet, and the posterior legs and feet 216 allow for the posterior leaflet to seal around them and make relatively normal contact with the anterior leaflet. In a diseased valve, there may be initial regurgitation, but is believed that the anchor 250 will have relatively little, if any, effect on the baseline valve function during the time that is implanted and prior to the implantation of the prosthetic valve. A covered embodiment of an anchor 250 is shown in FIG. 19 (atrial side of porcine mitral valve).

The requirements of the sealing interface with the native valve include ventricular to atrial sealing during systole, atrial to ventricular sealing during diastole, and stable chronic sealing that results from ingrowth incorporation of the sealing interface with the native valve. One approach to sealing is to utilize a native tissue engagement structure with the native leaflets along the annular perimeter to create a LV pressurized seal. This is not a mechanically compressive or attachment (active fixation) seal onto the native tissue. It also requires minimal or no radial expansion beyond the tissue engagement interface. In one contemplated embodiment of the percutaneous mitral valve, the frame is externally covered by tissue. During systole, the tissue expands radially reaching out to the native valve to create a paravalvular seal. The external tissue also expands radially on the atrial side cuff (outer covering on valve) to create a supra annular seal during systole.

Figure 20:
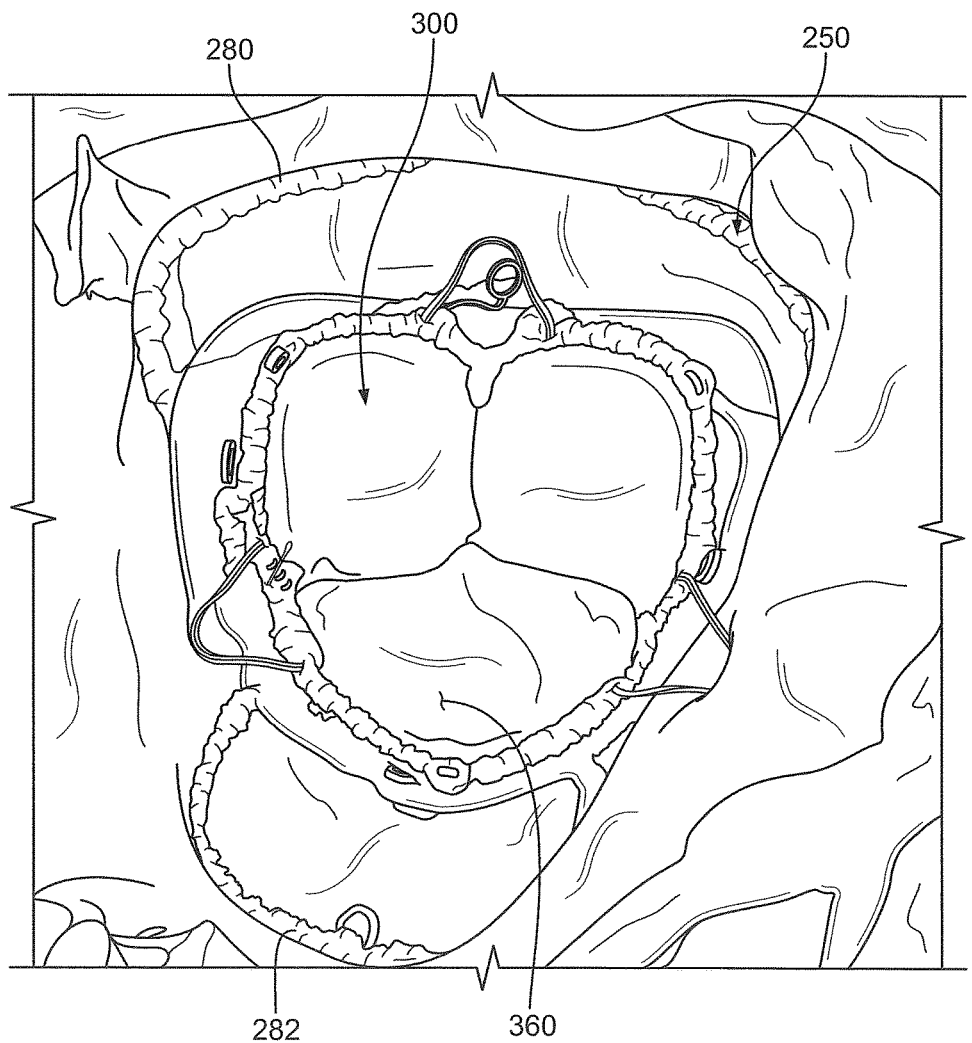
FIG. 20 depicts the anchor assembly of FIG. 19 having received a valve assembly from an atrial viewpoint.

As shown in FIG. 20, an anchor frame 250 covered with fabric can be placed proximate an annulus of a natural valve. A replacement valve assembly 300 is placed into engagement with the anchor 200. Thus, fabric such as Dacron of an anchor frame is placed adjacent native tissue on both ventricular and atrial sides of a valve annulus thereby facilitating a seal. A primary sealing mechanism is native leaflets sealing against prosthetic valve tissue. Dacron placed on feet can further facilitate sealing where there is ingrowth. Pericardial tissue (e.g. one or more of glutaraldehyde fixed ovine, equine, porcine or bovine pericardium having a thickness of 0.005"-0.036" inches, or 0.005"-0.014" inches) 360 is further provided on the valve assembly 300. The fabric of the anchor 200 interfaces with the biological tissue of the valve assembly 300. Moreover, the atrial position of the valve 300 is selected to facilitate a sealing surface such that the lower portion of the valve skirt 340 engages natural tissue (leaflets) around a periphery of the implant.

With respect to orientation/positioning methods, utilizing a separately implanted anchor substrate is the ability to utilize a fluoroscopic alignment technique to mesh the anchor with the valve. In this scenario, the x-ray fluoroscopic camera could be adjusted so a radiopaque (complete or interrupted around perimeter) anchor structure would be visualized in a relatively straight line (camera orientation—line connecting emitter with intensifier—is perpendicular to anchor circular axis, or parallel to plane of anchor ring). The valve frame structure could similarly have a radiopaque perimeter at the point at or near the interlock region with the anchor. When the anchor was viewed in the manner described, the valve axial orientation could be adjusted so the radiopaque perimeter was also a line (without moving camera position) meaning the two cylindrical axes of the anchor and valve were now parallel. Subsequently, the valve line could be appropriately positioned above, below, or at the interlock region. This linear alignment of the two radiopaque structures would be even more visually pronounced as the valve frame was being expanded/deployed, whether by balloon or self-expanding. This could additionally allow for fine tuning or adjustment prior to final engagement of the valve with the anchor structure.

General fluoroscopy based methods can be used to evaluate use of markers/overlays on a fluoro screen within the same camera/table position. It is noted that some equipment has built in marking capability within an image view. Further, device length markers in the form of a pigtail with 1 cm marks (useful in the Back view where pigtail is running through center of image) can be employed as can a wire with 1 cm marks along distal length, such as 1 cm marks on the pusher shaft. Further, dye injection methods are contemplated to better view sub-leaflet structure (with a curved diagnostic catheter placed sub-P2). Visible or augmented anatomic landmarks are of course to be considered including use of a guidewire in circumflex and tracking of the ICE probe or guidewire into coronary sinus. Finally, evaluations using echo LAX views to see leaflet tips in foot locations are contemplated.

Next addressed are general requirements for delivering a replacement mitral valve via a trans-septal approach, into a previously placed anchor. It is desirable that the valve be collapsed/compressed and encapsulated in some manner to navigate the venous system to the right atrium and to cross the inter-atrial septum and engage the native valve and the anchor retention structure in the disclosed embodiment. Also, given the relative stiffness of the collapsed valve assembly in this region, there may be a need for a flexible or possibly articulating segment proximal and possibly distal of the encapsulated valve region of the delivery system to aid with tracking. Further, the delivery system should be able to navigate a primary curve in the right atrium and trans-septal region of the anatomy. The system can then be able to navigate a secondary curve from the septum back toward the mitral valve, which may be out of plane relative the primary curve. The encapsulated valve can then also be able to be controllably expressed out of the catheter. In general, this can be accomplished via an advancement of the valve out of the catheter or via a pullback of an encapsulating sheath. The former requires significant adjustment and anticipation of final valve position as it is expressed. Unsheathing allows the valve to be in relative axial position prior to expression into the anchor structure. It may also be desirable during valve delivery to be able to reposition prior to full expression and deployment, primarily axially and to recapture or retrieval of the valve for removal prior to and after full expression and deployment. Moreover, it may be desirable for the delivery system to have temporary or releasable connections or holding points to control position as the valve begins to become loaded, as well as enable retrieval. Imaging visibility on fluoro and echo to facilitate alignment and positioning relative to native valve and the anchor of the disclosed embodiment is also contemplated. The alignment and positioning of the system includes axial position, rotational orientation, planar x-y position relative to native valve plane, and the axial vector relative to the perpendicular vector of the native valve plane.

Figure 21A:
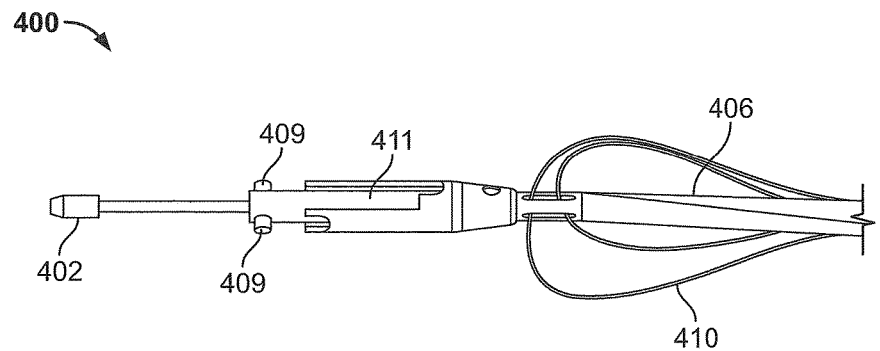
FIG. 21A depicts a partially collapsed anchor assembly mounted to a delivery catheter.
Figure 21B:
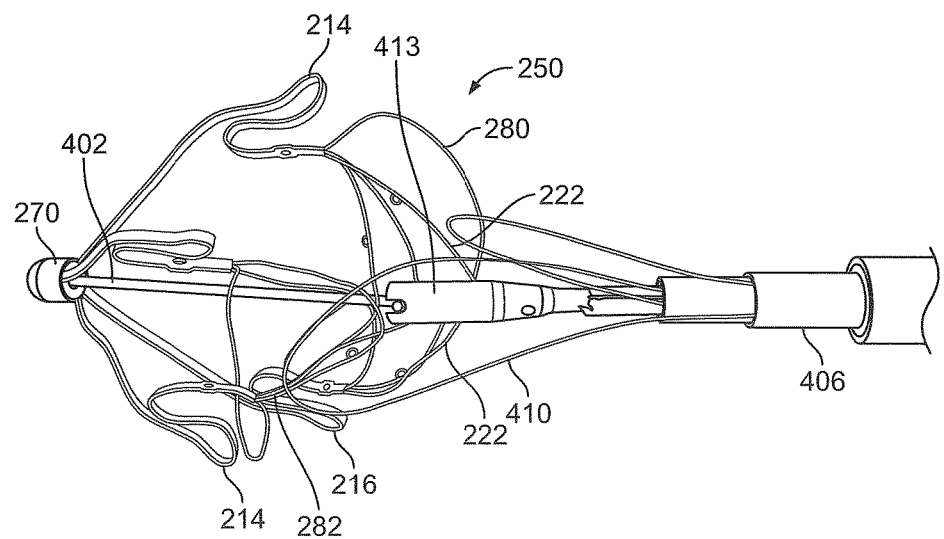
FIG. 21B depicts the expansion of the anchor assembly on FIG. 21A by the delivery catheter.
Figure 22A:
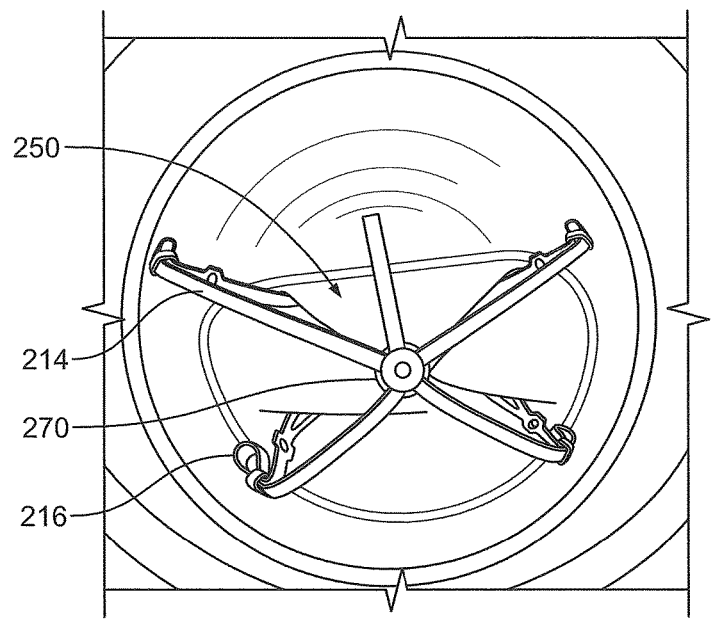
FIGS. 22A-D depict various views from a ventricular side of anchor retrieval.
Figure 22B:
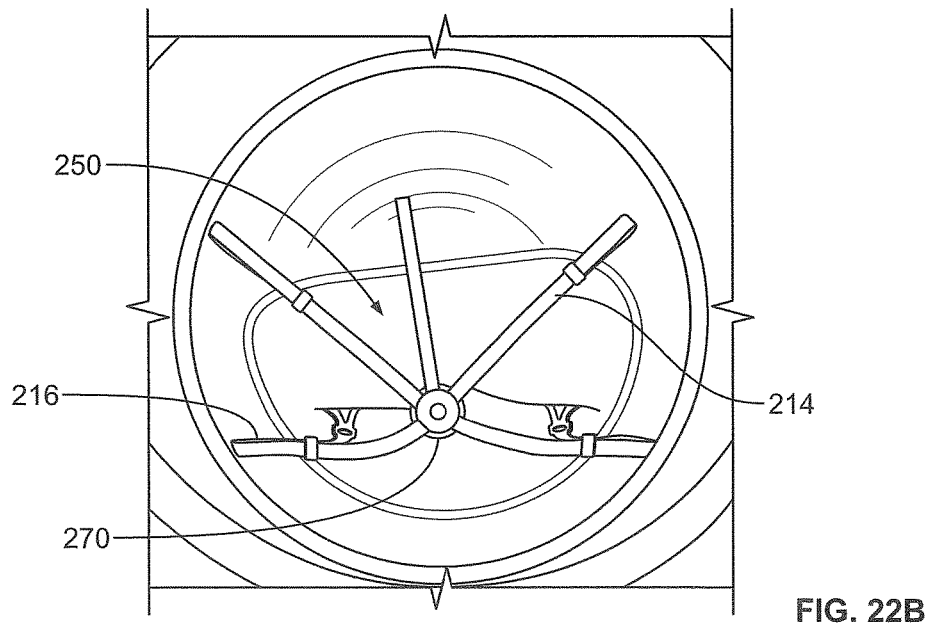
Figure 22C:
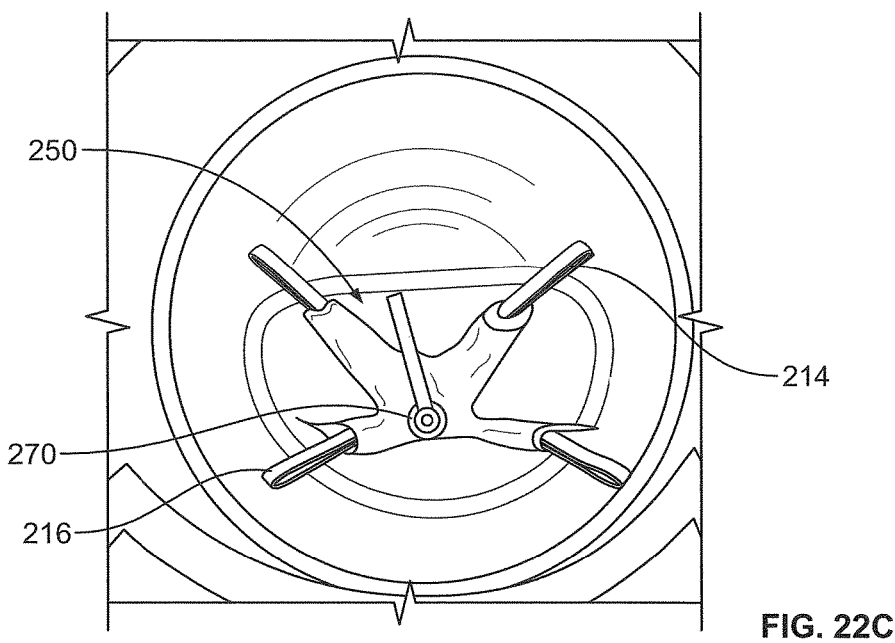
Figure 22D:
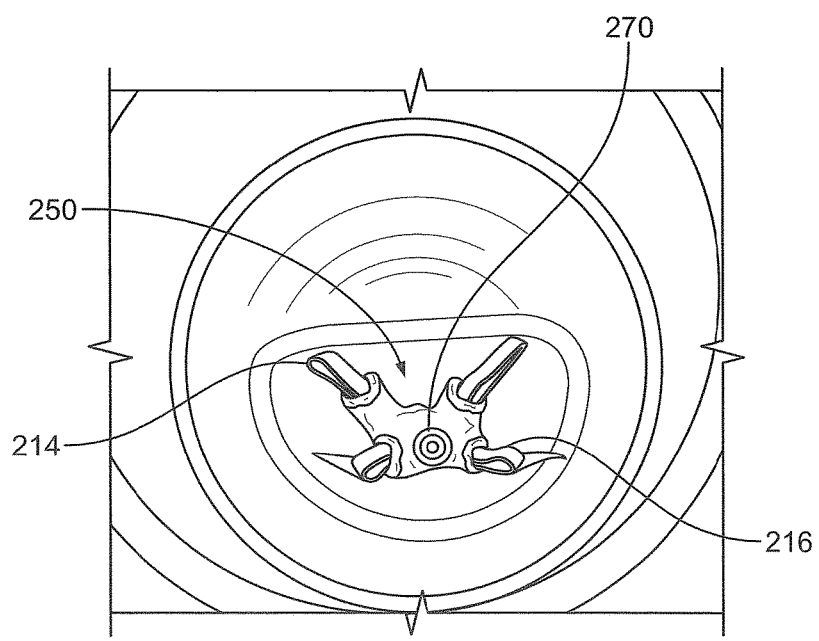
Figure 23A:
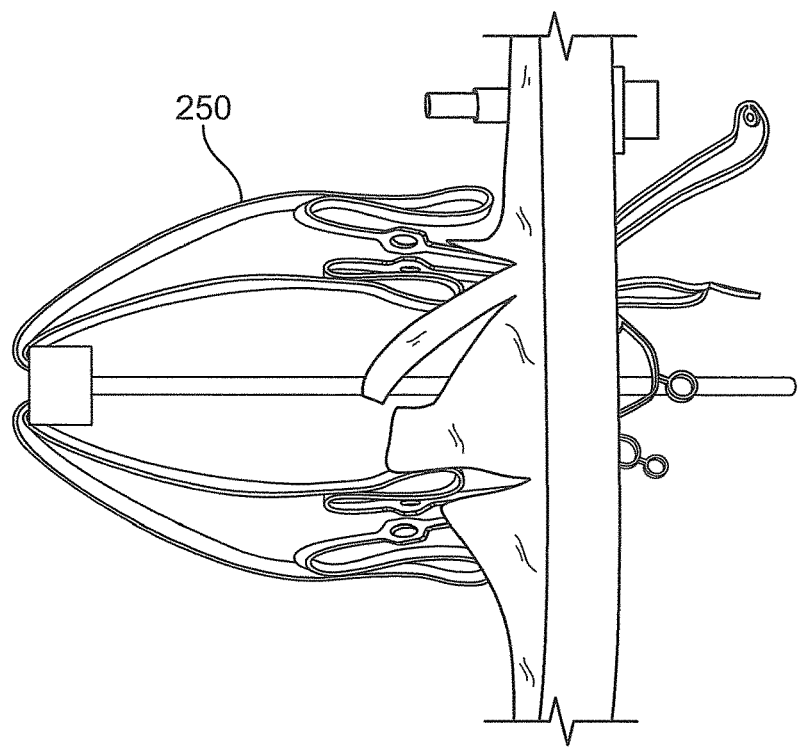
FIGS. 23A-E depict various side views depicting anchor retrieval.
Figure 23B:
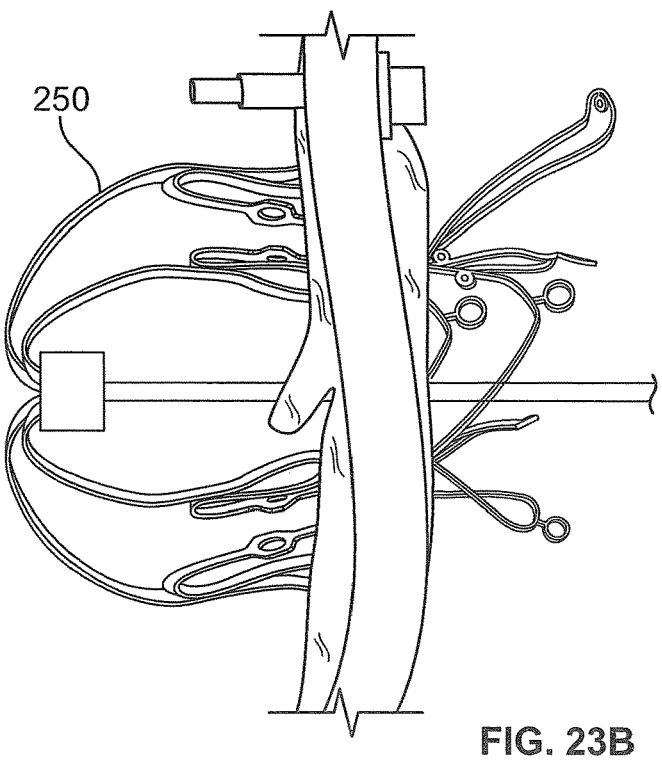
Figure 23C:
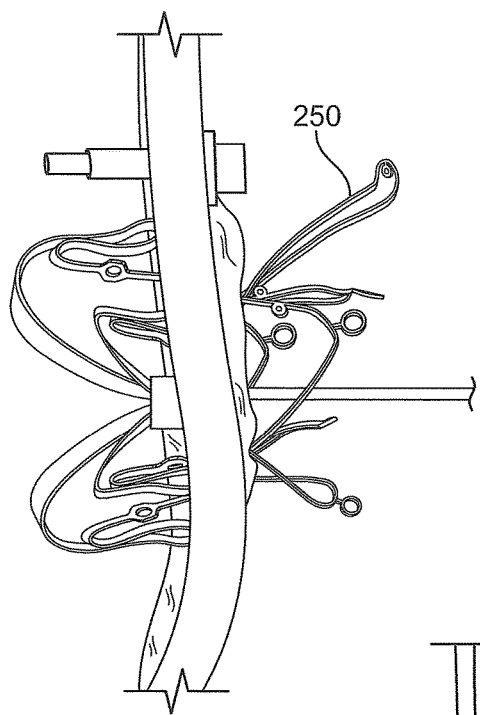
Figure 23D:
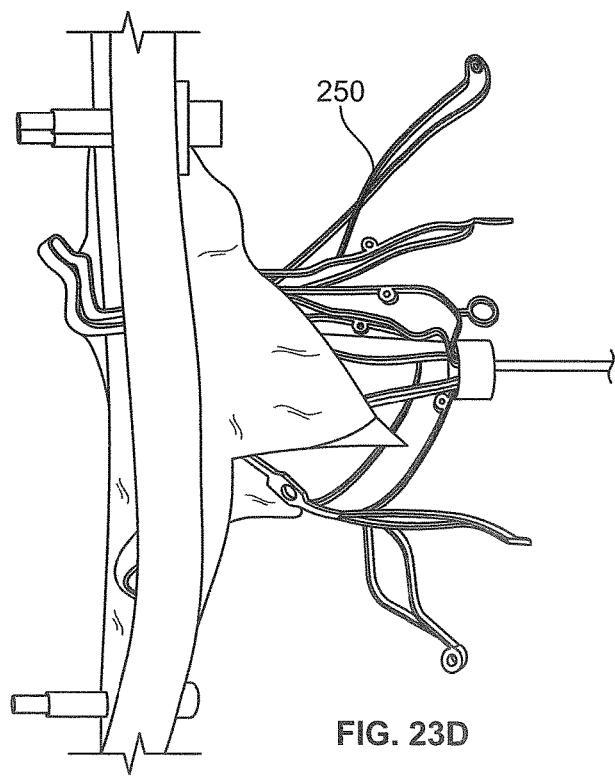
Figure 23E:
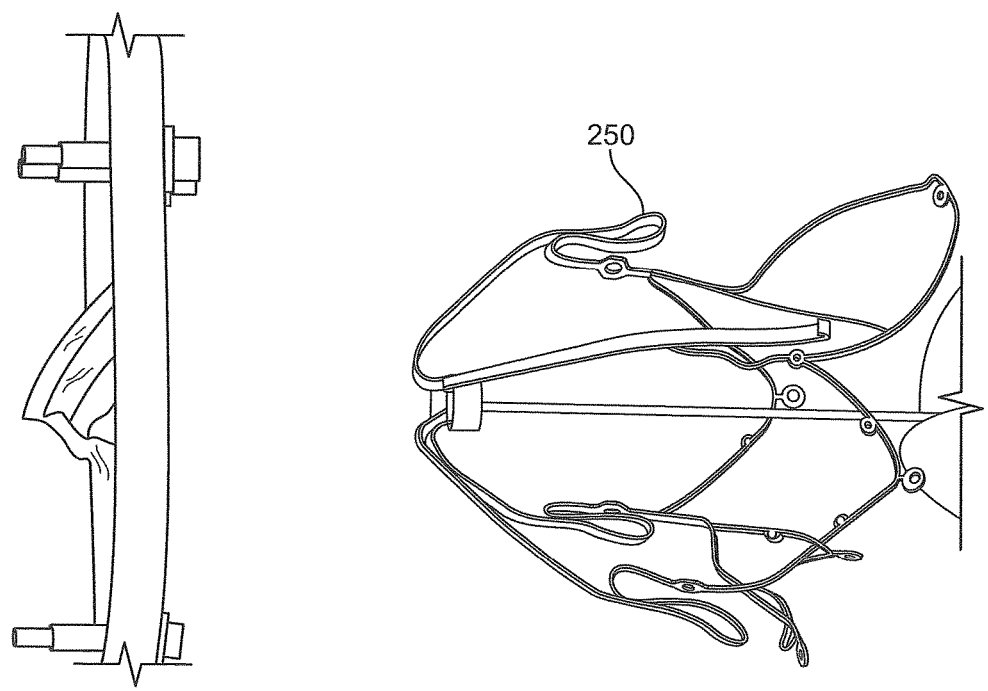

Turning now to certain aspects of a delivery structure there is shown in FIGS. 21A-B an anchor assembly 250 retained by a catheter 400. An outer delivery sheath configured to encompass the anchor 250 (not shown) is withdrawn, which may allow for partial diametric expansion of the anchor 250. The anchor 250 is elongated due to a push-rod 402 extended into a hub 270. The push rod 402 extends proximally through catheter shaft 406. Several releasable control features are further provided on various parts of anchor 250, including tethers 410 thread through atrial stabilization features 280, 282. Three of the four arches 222 of the frame connect to opposing distal posts 409, and a fourth arch 222 connects to a proximal post 411. The arches 222 extend within the interior of catheter shaft 406 keeping the arches under tension relative to the distal hub 270. The arch control elements can be covered with a tubular element 413 on the distal end of the catheter shaft 406. Withdrawing this tube 413 accomplishes coaxial expression of the anchor frame. Generally, the anchor 250 can be placed into the right atrium, then exposed, and at least partially expanded by retraction of push rod 402 relative to the catheter shaft 406.

As shown in FIG. 21B, anchor can then next be partially or completely expanded. At this time, it would be introduced across the native valve, then retracted to place feet 214, 216 within the gutter. The anchor 250 could be withdrawn by re-elongating and retracting, or if in desired position, the tethers 410 are released/removed, and the distal connection between the push rod 402 and hub 270 removed. This may be done, for example, by unscrewing a threaded arrangement between the push rod 402 and the hub 270. The last two control tethers 410, connecting to the atrial stabilization features 280, 282 can be released. However, removal of the anchor 250 is still possible by retraction of these tethers, which causes the anchor 250 to elongate against the anatomy, and the feet 214, 216 will fold back and allow removal of the anchor 250 into the atrium, and back into a delivery sheath or separate retrieval catheter.

In one particular approach (See FIGS. 22A-D and 23A-E), retrieval of an anchor 250 is contemplated via inversion. Thus, the anchor 250 can be retrieved by traction (if mispositioned, for example), by applying traction to the hub 270 and inverting the device back through the native valve. The feet 214, 216 are flexed backward. Following removal of the anchor 250 from the native valve and into the atrium, a separate capturing catheter (not shown) can be used to collapse the anchor and remove it from the atrium.

Figure 24A:
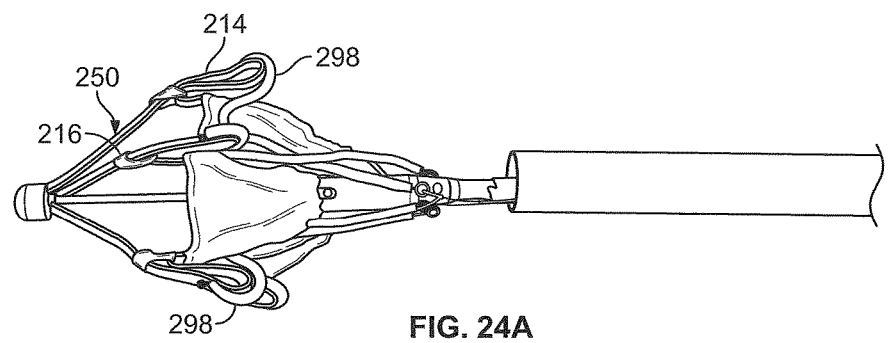
FIG. 24A depicts an anchor with retrieval skids.
Figure 24B:
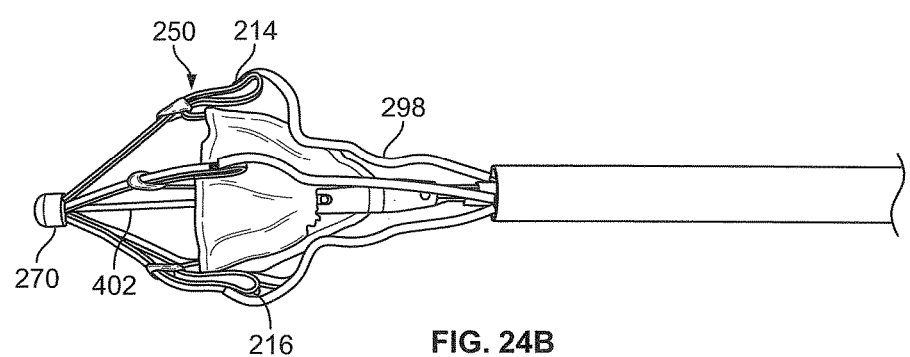
FIG. 24B depicts the anchor of FIG. 24A, with skids being used for traumatic retrieval.
Figure 24C:
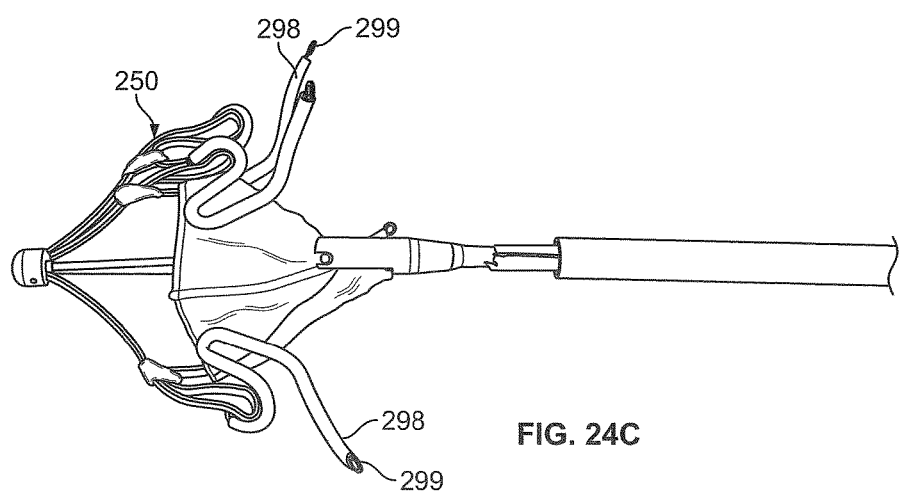
FIG. 24C depicts the anchor of FIG. 24A, with skids deployed.

In another approach (FIGS. 24A-C), retrieval and stabilization features can be incorporated into an anchor. For example, if the native leaflets are friable, a more atraumatic retrieval may be accomplished by adding retrieval skids 298 (4 are shown) to one or more of the feet 214, 216. The skids 298 follow the contour of the feet 214, 216, such that they are deployed behind the leaflet, just like the feet 214, 216. A portion of the skid structures 298 can extend superiorly, and may become atrial stabilization structures, once fully released (if retrieval is not performed). FIG. 24B depicts fully deployed skids 298, the superior portion of which extend out to become atrial stabilization features. At this point, the rest of the anchor 250 can be released from the delivery catheter and the delivery catheter can be removed. The skids 298 may be covered with ePTFE or other suitable covering to facilitate tissue ingrowth. Also note that eyelets 299 can be provided on superior ends of the skids 298, for use as delivery control points.

However, if retrieval is desired before full deployment and release of the anchor 250, the anchor 250 can be removed atraumatically upon extension of the pushrod. This elongates and straightens the skids 298, and pushes the valve leaflets (not shown) out of the way, allowing for the feet 214, 216 to be pulled back through the native valve without having to flex backward. The entire anchor can then be pulled into the delivery catheter, or a separate retrieval catheter.

Further modifications and alternative embodiments will be apparent to those of ordinary skill in the art in view of the disclosure herein. For example, the systems and the methods may include additional components or steps that were omitted from the diagrams and description for clarity of operation. Moreover, those of ordinary skill in the art will appreciate that aspects and/or features disclosed with respect to one embodiment in some cases may be incorporated in other embodiments even if not specifically described with respect to such other embodiments. It is to be understood that the various embodiments shown and described herein are to be taken as exemplary, including dimensions of various components, and as such various sizes outside of identified ranges are also contemplated. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims. Accordingly, this description is to be construed as illustrative only and is for the purpose of enabling those skilled in the art the general manner of carrying out the present teachings. It is to be understood that the particular examples and embodiments set forth herein are nonlimiting, and modifications to structure, dimensions, materials, and methodologies may be made without departing from the scope of the present teachings. Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

Thus, it will be apparent from the foregoing that, while particular forms of the invention have been illustrated and described, various modifications can be made without parting from the spirit and scope of the invention.

We claim:

1. A prosthetic mitral valve system configured to be implanted in multiple stages, comprising:
   an anchoring structure configured to be received adjacent a native mitral valve, the anchoring structure including sub-annular projections configured to engage a sub-annular commissural gutter of the native mitral valve, the anchoring structure including a retention structure configured to mate with an artificial valve assembly and to reside above an annulus of the native mitral valve, the retention structure comprising at least one supra-annular arch segment extending between adjacent sub-annular projections; and
   the artificial valve assembly configured to be implanted separately from the anchoring structure and to mechanically engage with said at least one supra-annular arch segment of the retention structure,
   wherein the artificial valve assembly has at least one upper arch segment configured to nest within said at least one supra-annular arch segment of the retention structure, and
   wherein a sub-annular portion of the anchoring structure includes an anti-SAM (systolic anterior motion) component that is configured to hinder systolic anterior motion (SAM) of a native mitral valve leaflet.

2. The system of claim 1, wherein the at least one supra-annular arch segment comprises a plurality of supra-annular arch segments, wherein each of the supra-annular arch segments extends between a respective pair of adjacent sub-annular projections such that the supra-annular arch segments form a continuous ring-like structure configured to mechanically engage with the valve assembly, and wherein the supra-annular arch segments are at least partially covered with fabric.

3. The system of claim 1, wherein the anchoring structure includes a central hub.

4. The system of claim 1, wherein the artificial valve assembly comprises:
   an external outer surface configured to mechanically engage within an internal space defined by the anchoring structure; and
   an annulus passageway smaller in diameter than the outer surface.

5. The system of claim 1, wherein the artificial valve assembly comprises an expandable frame with a stent structure having an inferior end and a superior end, the inferior end having a non-circular axial opening larger than a circular axial opening in the superior end.

6. The system of claim 5, wherein the artificial valve assembly comprises:
   three arches disposed at the superior end of the expandable frame, each arch having an apex at the superior end and defining three troughs therebetween:
   three posts attached to each trough respectively and extending in an inferior direction; and
   tissue attached to the three arches and three posts to define three leaflets of the artificial valve assembly.

7. The system of claim 1, wherein the anchoring structure includes a central hub from which the sub-annular projections extend.

8. A prosthetic mitral valve system configured to be implanted in multiple stages, comprising:
   an anchoring structure configured to be received adjacent a native mitral valve, the anchoring structure including sub-annular projections configured to engage a sub-annular commissural gutter of the native mitral valve, the anchoring structure including a retention structure configured to reside above an annulus of the native mitral valve, the retention structure comprising at least one supra-annular arch segment extending between adjacent sub-annular projections; and
   an artificial valve assembly configured to be implanted separately from the anchoring structure and to be received by the anchoring structure,
   wherein the at least one supra-annular arch segment comprises a plurality of supra-annular arch segments, wherein each of the supra-annular arch segments extends between a respective pair of adjacent sub-annular projections such that the supra-annular arch segments form a continuous ring-like structure configured to mechanically engage with the valve assembly,
   wherein the artificial valve assembly comprises an expandable frame with a stent structure having an inferior end and a superior end, the inferior end having a non-circular axial opening larger than a circular axial opening in the superior end,
   wherein at least one particular supra-annular arch segment of the plurality of supra-annular arch segments has first and second end portions, and wherein the retention structure further comprises a supra-annular atrial stabilization segment extending between the first and second end portions, and
   wherein the anchoring structure includes a central hub member from which two or more of the sub-annular projections extend.

9. The system of claim 8, wherein the anchoring structure comprises three supra-annular arch segments.

10. The system of claim 9, wherein the retention structure further comprises bridge supports extending between each pair of adjacent supra-annular arch segments.

11. The system of claim 8, wherein the artificial valve assembly comprises:
    an external outer surface configured to mechanically engage within an internal space defined by the anchoring structure; and
    an annulus passageway smaller in diameter than the external outer surface.

12. The system of claim 8, wherein the sub-annular projections are positioned outwardly away from the retention structure.

13. The system of claim 8, wherein the artificial valve assembly has at least one upper arch segment configured to nest within said at least one supra-annular arch segment of the retention structure.

14. A prosthetic mitral valve system configured to be implanted in multiple stages, comprising:
    an anchoring structure configured to be received adjacent a native mitral valve, the anchoring structure including sub-annular projections configured to engage a sub-annular commissural gutter of the native mitral valve, the anchoring structure including a retention structure configured to mate with an artificial valve assembly and to reside above an annulus of the native mitral valve, the retention structure comprising at least one supra-annular arch segment extending between adjacent sub-annular projections; and
    the artificial valve assembly configured to be implanted separately from the anchoring structure and to mechanically engage with said at least one supra-annular arch segment of the retention structure, wherein the artificial valve assembly has at least one upper arch segment configured to nest within said at least one supra-annular arch segment of the retention structure, and wherein a sub-annular portion of the anchoring structure includes an anti-SAM (systolic anterior motion) component at least partially covered by a fabric and including a portion for abutting a natural anterior leaflet to prevent the natural anterior leaflet from obstructing an aortic outflow tract.

15. The system of claim 14, wherein the anchoring structure comprises three supra-annular arch segments.

16. The system of claim 15, wherein the retention structure further comprises bridge supports extending between each pair of adjacent supra-annular arch segments.

17. The system of claim 14, wherein the anchoring structure includes a central hub.

18. The system of claim 14, wherein the artificial valve assembly comprises:

an external outer surface configured to mechanically engage within an internal space defined by the anchoring structure; and an annulus passageway smaller in diameter than the outer surface.

19. The system of claim 14, wherein the artificial valve assembly comprises an expandable frame with a stent structure having an inferior end and a superior end, the inferior end having a non-circular axial opening larger than a circular axial opening in the superior end.

20. The system of claim 19, wherein the artificial valve assembly comprises:

three arches disposed at the superior end of the expandable frame, each arch having an apex at the superior end and defining three troughs therebetween:

three posts attached to each trough respectively and extending in an inferior direction; and tissue attached to the three arches and three posts to define three leaflets of the artificial valve assembly.

\* \* \* \* \*